(12) United States Patent
Andrews et al.

(10) Patent No.: US 12,409,359 B2
(45) Date of Patent: Sep. 9, 2025

(54) EXERCISE DEVICE

(71) Applicant: F&P TECH FITNESS LIMITED, Auckland (NZ)

(72) Inventors: Ty Elgin Andrews, Hamilton (NZ); Louie George Heron, Hamilton (NZ); Raphael Jorge Millnitz Dos Santos, Hamilton (NZ); Russell Joseph Jackson, Hamilton (NZ); Anthony John Belsham, Hamilton (NZ); Craig Mounsey, Hamilton (NZ); James Laurence Van Oosten, Hamilton (NZ); Drew Patrick Marris, Hamilton (NZ)

(73) Assignee: F&P TECH FITNESS LIMITED, Auckland (NZ)

( * ) Notice: Subject to any disclaimer, the term of this patent is extended or adjusted under 35 U.S.C. 154(b) by 240 days.

(21) Appl. No.: 18/030,945

(22) PCT Filed: Oct. 8, 2021

(86) PCT No.: PCT/NZ2021/050171
§ 371 (c)(1),
(2) Date: Apr. 7, 2023

(87) PCT Pub. No.: WO2022/075864
PCT Pub. Date: Apr. 14, 2022

(65) Prior Publication Data
US 2023/0372766 A1    Nov. 23, 2023

(30) Foreign Application Priority Data

Oct. 8, 2020  (NZ) .................................. 768769
Aug. 25, 2021  (AU) ............................. 2021221561

(51) Int. Cl.
*A63B 21/00*    (2006.01)
*A63B 21/005*   (2006.01)
*A63B 24/00*    (2006.01)

(52) U.S. Cl.
CPC ........ *A63B 21/156* (2013.01); *A63B 21/0058* (2013.01); *A63B 21/153* (2013.01);
(Continued)

(58) Field of Classification Search
CPC ............ A63B 21/0053; A63B 21/0054; A63B 21/0058; A63B 21/0442; A63B 21/151;
(Continued)

(56) References Cited

U.S. PATENT DOCUMENTS 518,967 A * 5/1894 Poole .................. A63B 21/153
                                                    242/381.6
3,387,493 A * 6/1968 Strittmatter ............ A61B 5/221
                                                    73/862.471
(Continued)

FOREIGN PATENT DOCUMENTS

AU       2020345648 A1    4/2022
CN       111111107 A      5/2020
(Continued)

OTHER PUBLICATIONS

Extended European Search Report for European Patent Application No. 21878091.4 dated Sep. 30, 2024.

*Primary Examiner* — Gary D Urbiel Goldner
(74) *Attorney, Agent, or Firm* — Clark Hill PLC; James R. Foley

(57) ABSTRACT

A personal exercise device with a cable and resistance mechanism comprises a sensor arrangement configured to detect two orthogonal angles to define a trajectory of the cable extending in a 3-dimensional space during use. The sensor arrangement comprises a pulley to direct the cable as
(Continued)

it extends from the device during use, a cable follower through which the cable passes, the cable follower pivotally mounted to pivot about a first pivot axis and about a second pivot axis, the second pivot axis orthogonal to the first pivot axis, and wherein the first pivot axis is collinear with a rotational axis of the pulley, and one or more sensors configured to detect pivoting of the cable follower about the first and second pivot axes and provide one or more outputs indicative of the two orthogonal angles to define the trajectory of the cable extending in the 3-dimensional space.

21 Claims, 15 Drawing Sheets

(52) U.S. Cl.
CPC .. *A63B 24/0062* (2013.01); *A63B 2024/0093* (2013.01); *A63B 2220/16* (2013.01); *A63B 2220/833* (2013.01)

(58) Field of Classification Search
CPC . A63B 21/153; A63B 21/156; A63B 21/4035; A63B 21/4043; A63B 23/03508; A63B 23/03541; A63B 23/1209; A63B 24/0003; A63B 24/0062; A63B 24/0087; A63B 2024/0093; A63B 2071/027; A63B 2071/0683; A63B 2220/10; A63B 2220/16; A63B 2220/18; A63B 2220/40; A63B 2220/52; A63B 2220/833; A63B 2220/89; A63B 2225/20; A63B 2225/50
See application file for complete search history.

(56) References Cited

U.S. PATENT DOCUMENTS

| | | | |
|---|---|---|---|
| 3,610,617 A * | 10/1971 | Hepburn | A63B 21/015 482/116 |
| 3,690,654 A * | 9/1972 | Hepburn | A63B 21/153 482/909 |
| 3,764,132 A * | 10/1973 | Hepburn | A63B 21/00069 482/123 |
| 3,861,215 A * | 1/1975 | Bradley | A63B 21/00069 482/116 |
| 4,138,106 A * | 2/1979 | Bradley | A63B 21/00076 482/116 |
| 4,235,439 A * | 11/1980 | De Donno | A63B 21/00069 73/379.06 |
| 4,842,274 A * | 6/1989 | Oosthuizen | A63B 21/0058 482/901 |
| 4,848,152 A * | 7/1989 | Pratt, Jr. | A61B 5/1124 482/901 |
| 4,912,638 A * | 3/1990 | Pratt, Jr. | A63B 21/4005 600/595 |
| 4,979,733 A * | 12/1990 | Prud'Hon | A63B 21/153 482/901 |
| 5,015,926 A * | 5/1991 | Casler | A63B 21/00076 482/902 |
| 5,133,545 A * | 7/1992 | Moschetti | A63B 21/153 482/110 |
| 5,271,416 A | 12/1993 | Lepley | |
| 5,304,104 A * | 4/1994 | Chi | A63B 21/153 482/99 |
| 5,433,678 A * | 7/1995 | Chi | A63B 21/0058 482/99 |
| 5,643,157 A * | 7/1997 | Seliber | A63B 21/153 482/9 |
| 5,713,792 A * | 2/1998 | Ohzono | A63B 21/153 463/7 |
| 6,030,321 A * | 2/2000 | Fuentes | A63B 21/4013 482/74 |
| 6,280,361 B1 * | 8/2001 | Harvey | A63B 24/00 482/4 |
| 6,612,170 B2 * | 9/2003 | Brown | A63B 21/4043 73/379.06 |
| 7,163,488 B2 | 1/2007 | Anders et al. | |
| 7,775,936 B2 * | 8/2010 | Wilkinson | A63B 21/4035 482/8 |
| 8,075,453 B1 * | 12/2011 | Wilkinson | A63B 21/4019 482/8 |
| 8,900,099 B1 * | 12/2014 | Boyette | A63B 71/0619 482/901 |
| 9,539,458 B1 * | 1/2017 | Ross | A63B 21/4043 |
| 9,847,045 B2 | 12/2017 | Campolo et al. | |
| 10,220,235 B2 * | 3/2019 | Norris | A63B 21/153 |
| 10,220,261 B1 * | 3/2019 | Garsdean | A63B 24/0087 |
| 10,376,732 B2 * | 8/2019 | Garsdean | A63B 23/03525 |
| 10,434,368 B2 | 10/2019 | Chazalon et al. | |
| 10,617,904 B2 | 4/2020 | Chiavegato et al. | |
| 10,661,112 B2 * | 5/2020 | Orady | G01L 5/107 |
| 11,123,609 B2 * | 9/2021 | Rubin | A63B 21/4043 |
| 11,857,830 B2 * | 1/2024 | Stegeman | A63B 21/00061 |
| 12,208,304 B2 * | 1/2025 | Akeel | A63B 21/4035 |
| 2004/0204294 A2 * | 10/2004 | Wilkinson | A63B 22/203 482/52 |
| 2007/0155587 A1 * | 7/2007 | Huang | A63B 23/12 482/148 |
| 2010/0197462 A1 | 8/2010 | Piane, Jr. | |
| 2011/0237407 A1 * | 9/2011 | Kaleal | A63B 23/03541 482/114 |
| 2011/0287910 A1 * | 11/2011 | Ladd | A63B 21/153 482/133 |
| 2012/0053014 A1 * | 3/2012 | Zhu | A63B 21/4035 482/5 |
| 2013/0090216 A1 | 4/2013 | Jackson | |
| 2013/0267384 A1 * | 10/2013 | Eldridge | A63B 24/0062 482/5 |
| 2013/0310230 A1 * | 11/2013 | Norris | A63B 21/4035 482/115 |
| 2014/0038777 A1 * | 2/2014 | Bird | A63B 23/03525 482/5 |
| 2014/0121071 A1 | 5/2014 | Strom et al. | |
| 2014/0194250 A1 * | 7/2014 | Reich | A63B 24/0084 482/5 |
| 2014/0194251 A1 * | 7/2014 | Reich | A63B 21/00178 482/6 |
| 2014/0287876 A1 * | 9/2014 | Etter | A63B 24/0087 482/5 |
| 2017/0021215 A1 * | 1/2017 | Norris | A63B 21/153 |
| 2018/0001128 A1 * | 1/2018 | Norris | A63B 21/0058 |
| 2018/0021617 A1 * | 1/2018 | Krull | A63B 21/023 482/128 |
| 2018/0214729 A1 * | 8/2018 | Rubin | A63B 24/0087 |
| 2018/0280753 A1 * | 10/2018 | Krull | A63B 21/025 |
| 2019/0046830 A1 | 2/2019 | Chiavegato et al. | |
| 2019/0076691 A1 * | 3/2019 | Smith | A63B 23/1209 |
| 2019/0094090 A1 | 3/2019 | Hong et al. | |
| 2019/0168053 A1 * | 6/2019 | Garsdean | A63B 71/0622 |
| 2019/0344115 A1 | 11/2019 | Neuhaus et al. | |
| 2019/0344123 A1 | 11/2019 | Rubin et al. | |
| 2021/0205662 A1 * | 7/2021 | Berke | G08C 17/02 |
| 2021/0339078 A1 * | 11/2021 | Akeel | A63B 24/0087 |
| 2021/0353994 A1 * | 11/2021 | Paz Domonte | A63B 21/153 |
| 2021/0394011 A1 * | 12/2021 | Neuhaus | A63B 71/0622 |
| 2022/0001240 A1 * | 1/2022 | Rubin | A63B 24/0087 |
| 2022/0184445 A1 * | 6/2022 | Fortuin | A63B 24/0087 |
| 2022/0184452 A1 | 6/2022 | Valente et al. | |
| 2023/0405404 A1 * | 12/2023 | Belsham | A63B 21/0058 |

FOREIGN PATENT DOCUMENTS

| | | | | |
|---|---|---|---|---|
| EP | 3221015 B1 | 1/2019 | | |
| GB | 2562486 A | 11/2018 | | |
| KR | 20190061151 A | * | 6/2019 | ........... A63B 21/005 |
| WO | 2009/074942 A1 | | 6/2009 | |
| WO | WO-2010121337 A1 | * | 10/2010 | ........... A63B 21/153 |
| WO | 2014196866 A1 | | 12/2014 | |

(56) References Cited

FOREIGN PATENT DOCUMENTS

| WO | WO-2017223040 A1 | * | 12/2017 | ....... A63B 21/00069 |
|----|------------------|---|---------|----------------------|
| WO | 2020014667 A1 |  | 1/2020 |  |
| WO | 2021/046596 A1 |  | 3/2021 |  |

* cited by examiner

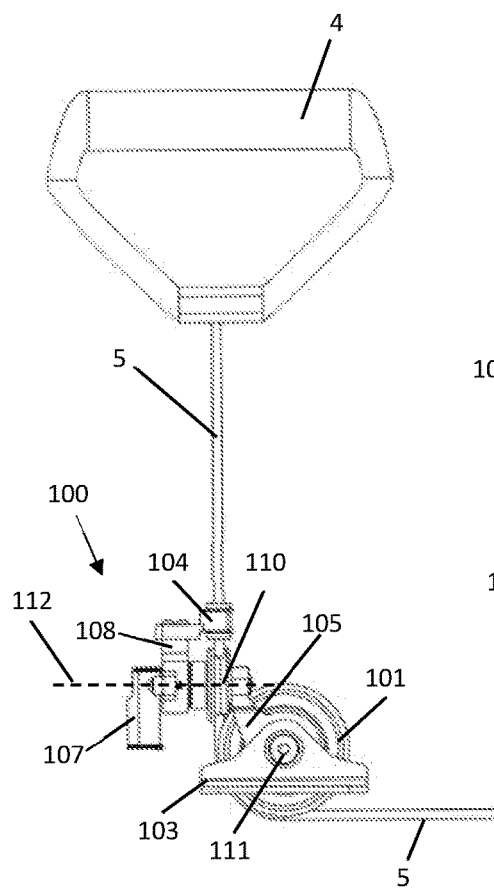
FIGURE 3C
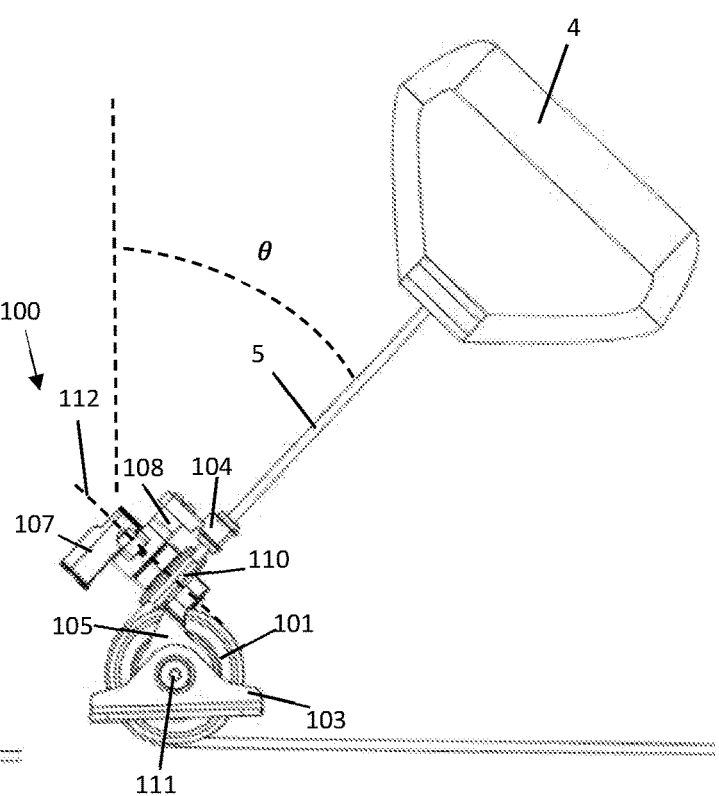
FIGURE 3D
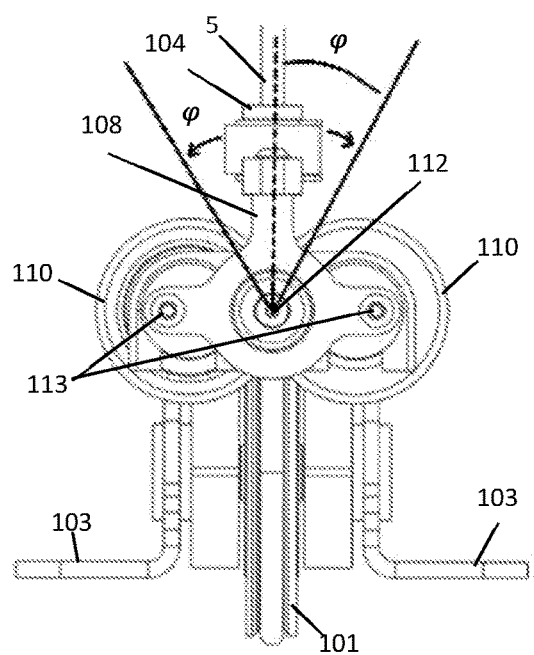
FIGRUE 3E

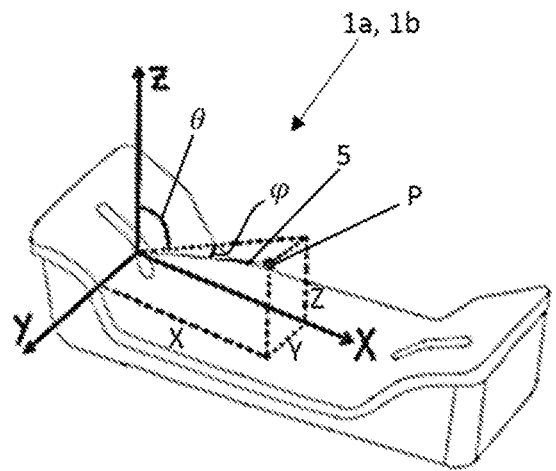
FIGURE 9
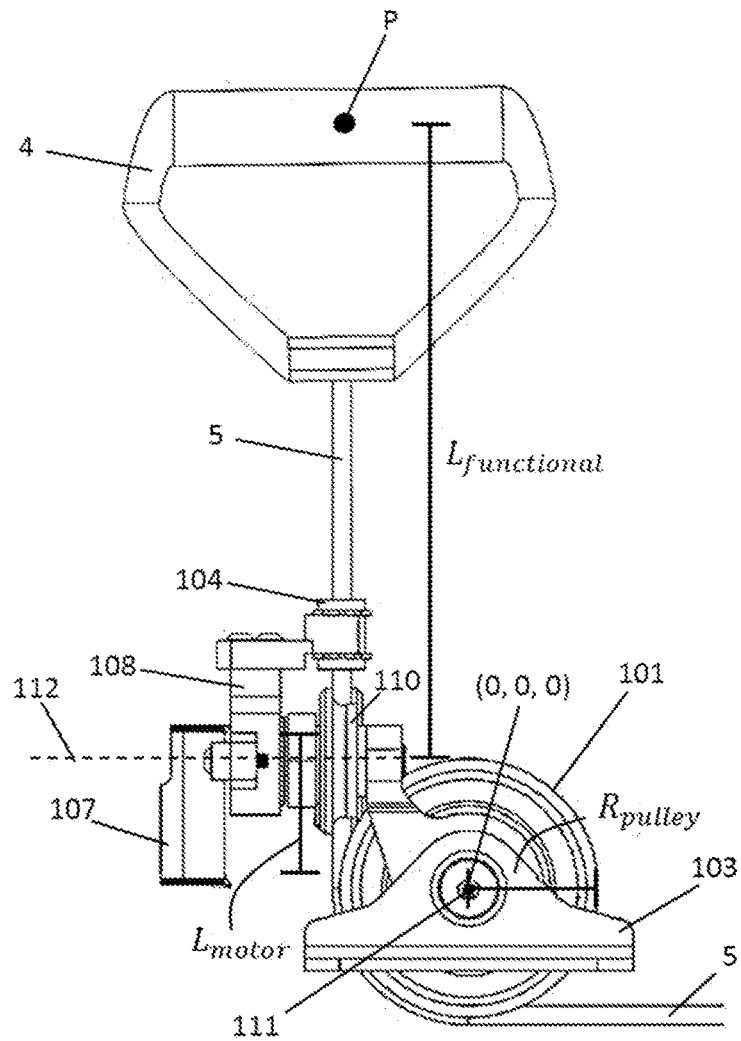
FIGRUE 10

EXERCISE DEVICE

STATEMENT OF CORRESPONDING APPLICATIONS

This application is a National Phase Filing of PCT/NZ2021/050171, having an International filing date of Oct. 8, 2021, which claims priority of NZ 768769, filed Oct. 8, 2020, and AU 2021221561, filed Aug. 25, 2021. The disclosure of the foregoing are hereby incorporated by reference.

FIELD OF INVENTION

The invention generally relates to the field of exercise devices that employ a user interface attached to a resistance mechanism via a cable to provide resistance training exercises to a user.

BACKGROUND TO THE INVENTION

Exercise equipment or devices for providing resistance-based exercises or training to a user traditionally include weights in the form of metal plates. Such exercise devices include a frame for movably supporting the plates, and a handle or bar or other user interface connected to the plates via a cable and pulley system for lifting the plates. A mechanism allows the user to select a desired number of plates in a stack and therefore weight to be lifted via the handle and cable to perform a weightlifting exercise.

Technological developments in areas such as electrical motor technology, display screen technology and digital camera technology have driven development of resistance-based exercise equipment that provides resistance training or exercise to a user via an electrically driven resistance mechanism. The electrically driven resistance mechanism (such as an electric motor/generator) may be controlled in a way to provide a resistance or force to the user that replicates a traditional stack of metal plates, to allow the user to perform familiar weight training exercises previously performed using traditional mechanical weight-based equipment.

One such example of an electrically driven resistance training device is the Tonal™ home gym.

One drawback of electrically driven resistance training devices is that they can be expensive. Devices may include one or more cameras to monitor the user, and a large display screen to present video or other visual information to the user, adding significant cost to the device. Cameras and screens may be required to monitor user performance and present performance or training feedback information to the user. Such systems may also require connection with a remotely located person (a personal trainer) via a communications network to provide feedback to the user during training.

While electrically driven resistance training devices may be much smaller and lighter than traditional mechanical metal plate systems, some electrical resistance-based exercise devices may not be portable, easily transported or moved. For example, such systems may be configured predominantly for indoor use, and/or may not be suitable for transporting from a home environment for use at an alternative venue such as a community gym, or in an outside environment such as park grounds or gardens.

SUMMARY OF THE INVENTION

It is an object of the invention to provide an exercise device that addresses one or more of the above-mentioned problems, and/or to provide the public with a useful choice.

According to a first aspect of the invention, the present invention provides an exercise device comprising:
 a user interface to be moved by a user in a 3-dimensional space when using the device;
 a resistance mechanism to generate a force;
 a cable coupled between the user interface and the resistance mechanism to transmit the force from the resistance mechanism to the user interface; and
 a sensor arrangement configured to detect two orthogonal angles to define a trajectory of the cable extending in the 3-dimensional space during use, the sensor arrangement comprising:
  a pulley to direct the cable as it extends from the device during use, the pulley comprising a rotational axis;
  a cable follower through which the cable passes, the cable follower pivotally mounted to pivot about a first pivot axis and about a second pivot axis, the second pivot axis orthogonal to the first pivot axis, and wherein the first pivot axis is collinear with the rotational axis of the pulley, and
  one or more sensors configured to detect pivoting of the cable follower about the first and second pivot axes and provide one or more outputs indicative of the two orthogonal angles to define a trajectory of the cable extending in the 3-dimensional space.

In some embodiments, the cable follower is mounted on a pivoting frame, the pivoting frame pivotally mounted to pivot on the rotational axis of the pulley.

In some embodiments, the pivoting frame and the pulley are mounted together on a single axle.

In some embodiments, the cable follower is pivotally mounted to the pivoting frame to pivot relative to the pivoting frame about the second pivot axis.

In some embodiments, the pulley is a lower pulley, and the sensor arrangement further comprises a pair of upper pulleys rotationally mounted to the pivoting frame between the cable follower and the lower pulley, to guide the cable to extend from the lower pulley in a central plane of the lower pulley.

In some embodiments, the second pivot axis is aligned with a central plane of the pulley.

In some embodiments, the second pivot axis is positioned on a lower pulley side of a line extending between the rotational axes of the upper pulleys (i.e. the second pivot axis is below the rotational axes of the upper pulleys).

In some embodiments, the lower pulley, pivoting frame and cable follower are pivotally mounted on one or more pivot mounts to pivot about the second pivot axis.

In some embodiments, the pulley and pivoting frame are mounted on an axle supported by one or more axle supports, and the one or more axle supports are mounted to the pivot mounts to pivot on the second pivot axis.

In some embodiments, the sensor arrangement comprises two said pivot mounts spaced apart and with the one or more axle supports mounted thereon and with the pulley located between two pivot mounts.

In some embodiments, a first one of said pivot mounts is located on the resistance mechanism side of the pulley and is configured to receive the cable extending on a resistance mechanism side of the pulley therethrough so that the cable extends on a pivot axis of the first pivot mount.

In some embodiments, each pivot mount provides a base to mount the sensor arrangement to a surface extending below the pulley.

In some embodiments, the sensor arrangement is mounted within a recess in a top of a housing of the device, with the pivot mounts housed inside the housing, the sensor arrangement extending between two opposed sides of the recess via an aperture in each opposed side of the recess.

In some embodiments, the recess provides an open area on either side of the sensor arrangement through the housing of the device so that any debris or liquid entering the recess can pass through the recess to below the device.

In some embodiments, the sensor arrangement comprises a second frame, the second frame comprising the one or more axle supports and a pair of aligned spigots, each spigot pivotally supported at a respective pivot mount.

In some embodiments, a pivoting assembly comprising the pulley, pivoting frame and cable follower is weighted so that the centre of gravity of the pivoting assembly is at the second pivot axis, such that the pulley remains in a last orientation about the second pivot axis when tension applied by a user to the cable is removed during use.

In some embodiments, a first angle is an angle of the cable follower in a first plane perpendicular to the rotational axis of the pulley.

In some embodiments the first plane pivots on the second pivot axis with the pulley.

In some embodiments the first angle is indicative of an angle of wrap of the cable about the pulley.

In some embodiments a second angle of the cable follower is an angle in a vertical second plane orthogonal to the first plane, between the first plane and a vertical plane that intersects the first plane at the second pivot axis.

In some embodiments, the one or more sensors comprises:
  a first sensor configured to detect the pivoting of the cable follower about the first pivot axis and provide an output indicative of the first angle of the cable, and
  a second sensor configured to detect the pivoting of the cable follower about the second pivot axis and provide an output indicative of the second angle of the cable.

In some embodiments, the sensor arrangement comprises gears between the pivoting frame and the first sensor or a sensor element sensed by the first sensor, the gears providing an increasing gear ratio from the pivoting frame to the first sensor or the sensor element.

In some embodiments, the first sensor and the second sensor are mounted together.

In some embodiments, the sensor arrangement comprises limit stops to limit the amount of pivoting of the cable follower about the first pivot axis and/or second pivot axis.

In some embodiments, the pivoting frame comprises a first surface to abut a corresponding surface on at least one axle support or the second frame to limit the pivoting of the cable follower in a first direction of rotation about the first pivot axis. In some embodiments, the pivoting frame comprises a second surface to abut a corresponding surface on at least one axle support or the second frame to limit the pivoting of the cable follower in a second opposite direction of rotation about the first pivot axis.

In some embodiments, the axle supports or the second frame comprises a first surface to abut a corresponding surface on at least one pivot mount to limit the pivoting of the cable follower in a first direction of rotation about the second pivot axis.

In some embodiments, the axle supports or the second frame comprises a second surface to abut a corresponding surface on at least one pivot mount to limit the pivoting of the cable follower in a second opposite direction of rotation about the second pivot axis In some embodiments, the second pivot axis is collinear with the cable extending on a resistance mechanism side of the pulley.

In some embodiments, the resistance mechanism comprises an electric motor and a spool rotationally driven by the motor, and wherein the cable is coupled to the spool; and the device comprises a motor controller configured to operate the motor to generate the force.

In some embodiments, the device comprises a position sensor and a system controller configured to determine:
  a length of cable extending in the 3-dimensional space based on one or more outputs from the position sensor;
  the two orthogonal angles based on the one or more outputs from the one or more sensors; and
  a position of the user interface in the 3-dimensional space during use based on the length of the cable and the two orthogonal angles.

In some embodiments, the position sensor provides one or more outputs indicative of a rotational position of the motor and/or spool and the length of the cable is based on the motor and/or spool position and a diameter of the spool.

In some embodiments, the controller is configured to determine a coordinate in a coordinate system for the user interface position in the 3-dimensional space.

In some embodiments, the controller is configured to determine the coordinate based on an origin for the coordinate system that is positioned at or with respect to the rotational axis of the pulley or a vertical bottom of the pulley.

In some embodiments, the controller is configured to determine the length of the cable and/or a coordinate for the user interface in the 3-dimensional space based on an angle of wrap of the cable about the pulley.

In some embodiments, the controller is configured to determine the length of the cable with respect to a vertical bottom of the pulley.

In some embodiments, an origin for the sensor(s) for measuring the two orthogonal angles of the cable is at the second pivot axis.

In some embodiments, the system controller is configured to provide feedback to the user via a feedback device based on the position of the user interface in the 3-dimensional space.

In some embodiments, the one or more sensors comprises an inertial measurement unit.

In a preferred embodiment, the device comprises a deck or platform upon which a user stands when using the device, and:
  a pair of said user interfaces,
  a pair of said resistance mechanisms each configured to generate a force,
  a pair of said cables, each cable coupled between a respective user interface and resistance mechanism, and
  a pair of said sensor arrangements, each sensor arrangement configured to provide one or more outputs indicative of the two orthogonal angles of a respective cable.

Preferably device comprises a pair of positions sensors and a system controller configured to determine:
  a length of each cable extending in the 3-dimensional space based on one or more outputs from each respective position sensor;
  the two orthogonal angles of each cable based on the one or more outputs from the respective sensor arrangement, and
  a position of each user interface in the 3-dimensional space during use based on the length and the two orthogonal angles of the respective cable.

Preferably each resistance mechanism comprises an electric motor and a spool rotationally driven by the motor, and wherein the respective cable is coupled to the spool; and each position sensor provides one or more outputs indicative of a rotational position of the respective motor and/or spool and the length of the cable is based on the motor and/or spool position and a diameter of the spool.

According to a second aspect of the invention, the present invention provides a method for determining a position of a user interface of a personal exercise device in a 3-dimensional space during use, the exercise device comprising:

the user interface, a resistance mechanism to generate a force, a cable coupled between the user interface and the resistance mechanism to transmit the force from the resistance mechanism to the user interface, and a pulley directing the cable from the exercise device in the 3-dimensional space, and a cable follower through which the cable passes, the cable follower pivotally mounted to pivot about a first pivot axis and about a second pivot axis, the second pivot axis orthogonal to the first pivot axis;

wherein the method comprises:

determining a length of cable extending in the 3-dimensional space;

determining two orthogonal angles of the cable to define a trajectory of the cable extending in the 3-dimensional space based on pivoting of the cable follower about the first and second pivot axes; and determining the position of the user interface in the 3-dimensional space during use based on the length of the cable and the two orthogonal angles.

In some embodiments, the method comprises determining a coordinate in a coordinate system for the user interface position in the 3-dimensional space.

In some embodiments, the method comprises determining the coordinate based on an origin for the coordinate system that is positioned at or with respect to the rotational axis of the pulley or a vertical bottom of the pulley.

In a most preferred embodiment, the method comprises determining the length of the cable and/or a coordinate for the user interface in the 3-dimensional space based on an angle of wrap of the cable about the pulley.

In some embodiments, the method comprises determining the length of the cable with respect to a vertical bottom of the pulley.

In some embodiments, the method comprises determining the two orthogonal angles of the cable with respect to an origin, wherein the origin is at the second pivot axis.

According to a third aspect of the invention, the present invention provides a sensor arrangement configured to detect two orthogonal angles to define a trajectory of a cable extending in a 3-dimensional space, the sensor arrangement comprising:

a pulley to direct the cable to extend in the 3-dimensional space, the pulley comprising a rotational axis;

a cable follower through which the cable passes, the cable follower pivotally mounted to pivot about a first pivot axis and about a second pivot axis, the second pivot axis orthogonal to the first pivot axis, and wherein the first pivot axis is collinear with the rotational axis of the pulley, and one or more sensors configured to detect pivoting of the cable follower about the first and second pivot axes and provide one or more outputs indicative of the two orthogonal angles to define the trajectory of the cable extending in the 3-dimensional space.

The sensor arrangement of the third aspect of the invention may comprise any one or more of the features of the sensor arrangement described above with reference to the first aspect of the invention.

According to a fourth aspect of the invention, the present invention provides a personal exercise device comprising:

a user interface to be moved by a user in a 3-dimensional space when using the device;

a resistance mechanism to generate a force;

a cable coupled between the user interface and the resistance mechanism to transmit the force from the resistance mechanism to the user interface; and a sensor arrangement configured to detect two orthogonal angles to define a trajectory of the cable extending in the 3-dimensional space during use, the sensor arrangement comprising:

a pulley to direct the cable as it extends from the device during use, the pulley comprising a rotational axis;

a cable follower through which the cable passes, the cable follower pivotally mounted to pivot in a first vertical plane about a first pivot axis when the sensor arrangement is oriented with the cable follower positioned in the first vertical plane, and in a second vertical plane about a second pivot axis when the sensor arrangement is oriented with the cable follower positioned in the second vertical plane, the second pivot axis orthogonal to the first pivot axis, and the second vertical plane orthogonal to the first vertical plane, and wherein the first pivot axis is collinear with the rotational axis of the pulley, and one or more sensors configured to detect pivoting of the cable follower about the first and second pivot axes and provide one or more outputs indicative of an angle of the cable in the first vertical plane when the sensor arrangement is oriented with the cable follower positioned in the first vertical plane and an angle of the cable in the second vertical plane when the sensor arrangement is oriented with the cable follower positioned in the second vertical plane.

In some embodiments, the first angle is detected or determined in a first pivoting plane that pivots from vertical about the second pivot axis, the first pivoting plane orthogonal to the rotational axis of the pulley. In some embodiments, the cable follower pivots away from the second vertical plane about the first pivot axis and the second angle of the cable follower is determined or detected in the second vertical plane. In such an embodiment, the second pivot axis is fixed relative to the first pivot axis.

In some embodiments, the first vertical plane is fixed in the vertical orientation. In some embodiments, the cable follower pivots away from the second vertical plane about the first pivot axis and the second angle of the cable follower is detected or determined in a plane tangential to the pulley in which the cable follower pivots about the second pivot axis. In such an embodiment the second pivot axis pivots about the first pivot axis.

The device of the fourth aspect of the invention may comprise any one or more of the features of the device described above with reference to the first aspect of the invention.

Unless the context clearly requires otherwise, throughout the description and the claims, the term 'handle' is intended to mean a component to be grasped by a user and/or otherwise engage a user's hand, foot or body, such as, a bar, hand grip, hoop, strap, or any other suitable piece of equipment enabling a person to apply tension to a cable attached to the component or 'handle' via the user's hand, foot or body. Such a handle or component may therefore be described as a 'user interface'.

Unless the context clearly requires otherwise, throughout the description and the claims, the term 'extend vertically' (or similar terms such as extending vertically) is intended to mean the cable extends in a direction with a significant or predominant vertical component (and may include a horizontal component).

Unless the context clearly requires otherwise, throughout the description and the claims, where more than one controller is described, such as a motor controller and a system controller, one skilled in the art will understand the more than one controller may be implemented by a single controller, such as a single electronic processor. Conversely, where a controller such as a system controller is described, such a controller may be implemented by one or more than one controller, such as two or more electronic processors in electrical communication. One or controllers may be provided remotely.

The term 'cable' is intended to mean any flexible elongate member capable of transmitting tension, such as a cable, cord, strap, webbing etc., and is not intended to be limited to any particular construction or cross section. For example, a 'cable' described herein could be in the form of a length of webbing with a flat cross section.

Throughout the specification and claims, where one or more sensors provide(s) one or more outputs from which a value or parameter can be determined (such as an angle or position), the one or more outputs are said to be indicative of the value or parameter.

Throughout the specification and claims, terms such as "above" and "below" are used in a relative sense and are not intended to be limiting. One skilled in the art will understand that an arrangement or assembly as described with such relative terms may be inverted so that "above" becomes "below" and vice versa.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which:

FIG. 3C provides a side view of the sensor arrangement of FIG. 3A, cable and handle of the device with the cable extending vertically;

FIG. 3D provides a side view of the sensor arrangement of FIG. 3A, cable and handle of the device with the sensor arrangement oriented with the cable extending at an angle to vertical in a vertical first plane;

FIG. 3E provides an end view of the sensor arrangement of FIG. 3A oriented with the cable extending vertically in a vertical second plane orthogonal to the vertical first plane and indicates an angle between the vertical first plane and a possible trajectory of the cable in the vertical second plane (a sensor is omitted from FIG. 3E);

FIG. 9 provides a schematic representation of the devices of FIGS. 1A, 1B and 6 indicating a coordinate system for the position of a handle of the devices in a 3-dimensional space during use;

FIG. 10 provides an enlarged version of FIG. 3C including nomenclature for parameters used in equations disclosed herein for determining a position of the handle in a 3-dimensional space;

BRIEF DESCRIPTION OF PREFERRED EMBODIMENTS OF THE INVENTION

Figure 1A:
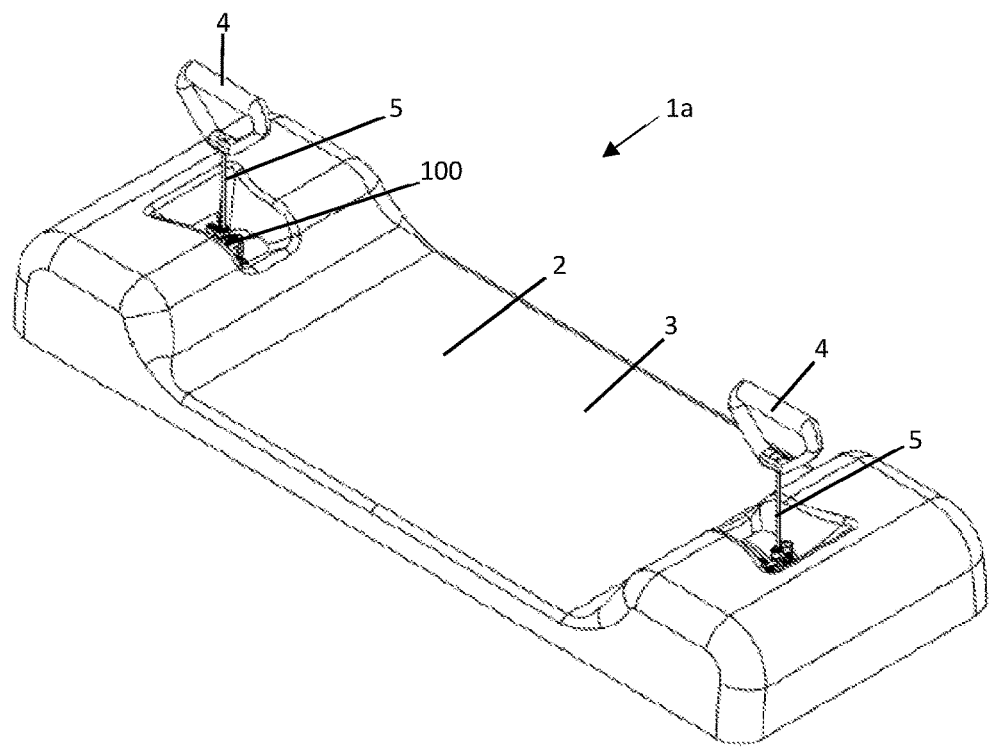
FIG. 1A illustrates one embodiment of an exercise device according to an aspect of the present invention.
Figure 1B:
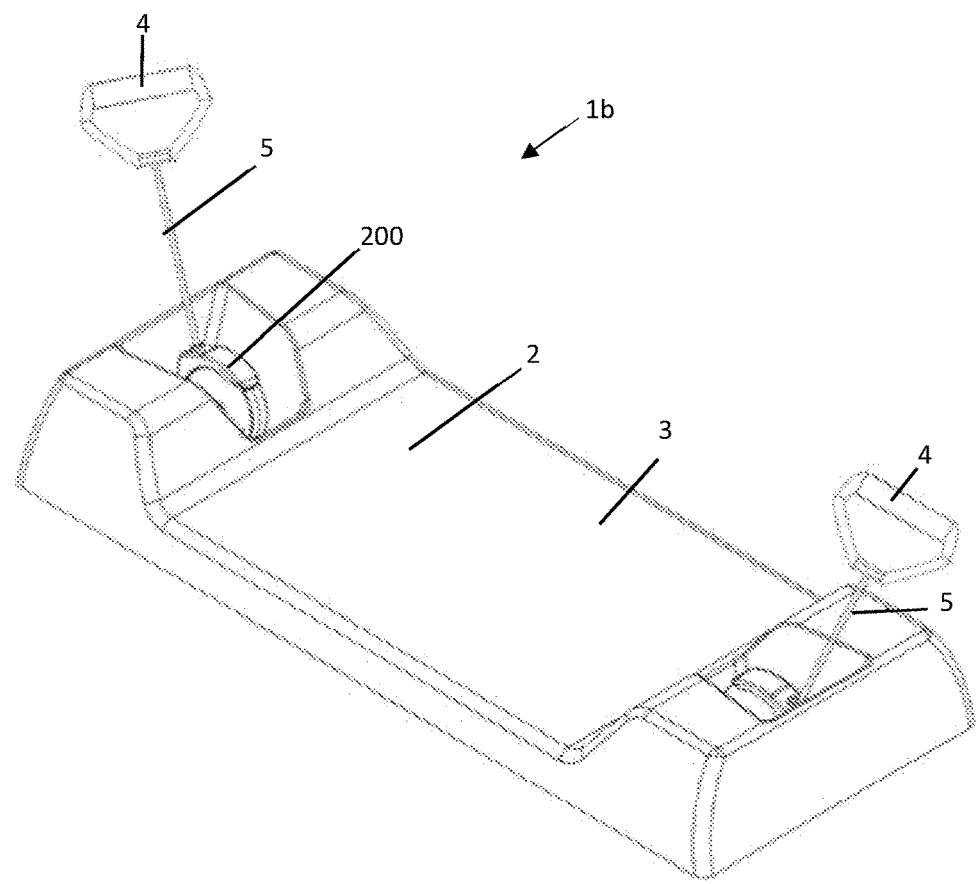
FIG. 1B illustrates another embodiment of an exercise device according to an aspect of the present invention.

FIGS. 1A and 1B show two example embodiments of a resistance exercise device according to one or more aspects of the present invention. Each device 1a, 1b comprises a frame or housing 2 (herein housing) to house or contain or mount various components of the device 1a, 1b. In the illustrated embodiments the housing 2 presents a deck or platform 3 upon which a user stands when using the device 1a, 1b. A pair of user interfaces (herein 'handles') 4 are provided to be gripped by the user. Each handle 4 is connected to a respective flexible elongate member (herein 'cable') 5 extendable from and retractable into the housing 2. Each cable 5 is coupled to a resistance mechanism (hidden from view in FIGS. 1A and 1B) mounted within the housing 2 to provide resistance to the user via the cables 5 and handles 4 as the user lifts the handles 4 to extend the cables 5 from the housing 2 and lowers the handles 4 towards the housing 2.

The resistance mechanism (described below) provides a force or resistance (force) to a respective cable 5. The cable 5 is coupled between the resistance mechanism and the handle 4 to transmit the force from the resistance mechanism to the user via the handle 4 with the cable in tension. When the user provides a force to the handle 4 that is greater than the force provided to the cable 5 by the resistance mechanism, the user lifts the handle 4 and extends the cable 5 from the housing 2. When the user provides a force to the handle 4 that is less than the force provided by the resistance mechanism to the cable 5, the resistance mechanism retracts the cable 5 into the housing 2 as the user lowers the handle 4 towards the housing 2.

Figure 2A:
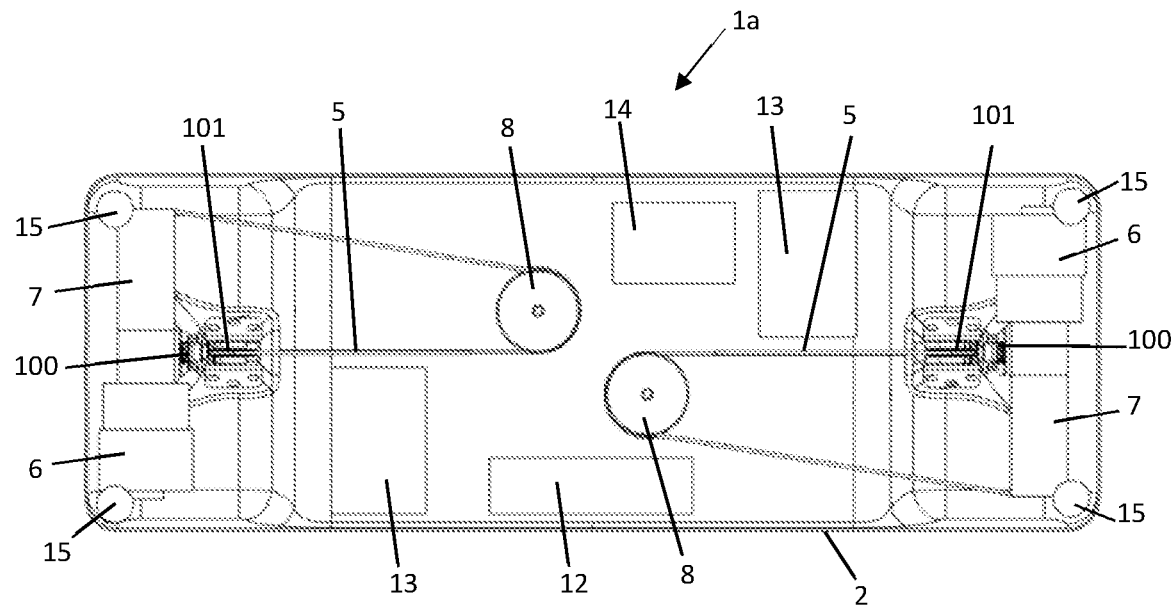
FIG. 2A is a bottom view of the device of FIG. 1A to show various components of the device mounted within a housing of the device.

FIG. 2A provides a bottom view of the device 1a of FIG. 1A with a bottom cover removed to show internal components of the device 1a. The resistance mechanism comprises an electric motor 6 and a spool 7 coupled to the motor 6 on which the cable 5 wraps and unwraps as the cable 5 is retracted into the housing 2 and extended from the housing during use. In this illustrated embodiment, the spool 7 is directly coupled to the motor, for example a shaft of the motor is directly coupled to the spool, with a rotational axis of the spool collinear with a rotational axis of the motor. To achieve a low-profile deck or housing, the motor 6 and spool 7 are arranged towards one end of the device 1a. The cable 5 extends from the spool 7 and passes around a first pulley 8 to align the cable 5 with an opening through the housing. The cable 5 extends from the first pulley 8 in a substantially horizontal plane. The cable 5 passes around a second pulley 101 to orient the cable from extending horizontally below the deck 3 or top surface of the housing 2 to extend vertically through the opening in the housing 2. In the illustrated embodiment, the motor 6 and spool 7 have a horizontal axis, the first pulley 8 has a vertical axis, and the second pulley 101 has a horizontal axis.

The arrangement of the cable 5, motor 6, spool 7 and pullies 8, 101 is replicated at each end of the device 1a, to provide force to two handles 4 of the device 1a. One skilled in the art will understand that in some embodiments, only one motor, spool, cable and pulley set may be provided to provide force to a single handle of the device. In such an embodiment, the cable may extend through a centrally located opening in the deck/housing 2.

Figure 2B:
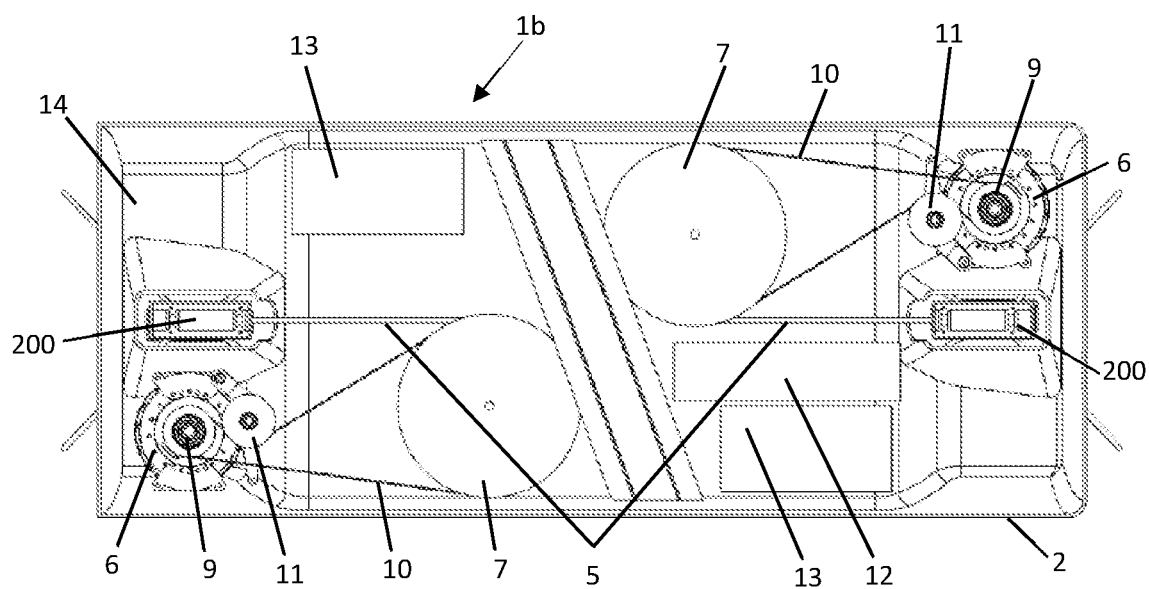
FIG. 2B is a bottom view of the device of FIG. 1B to show various components of the device mounted within a housing of the device.

FIG. 2B provides a bottom view of the device 1b of FIG. 1B with a bottom cover removed to show internal components of the device 1b. In this embodiment, the motor 6 is mounted with a rotational axis of the motor oriented vertically. The motor 6 drives rotation of a spool 7 via a drive pulley 9 directly coupled to the motor 6 and a belt 10 extending between the drive pulley 9 and the spool 7. An idler pulley 11 tensions the belt 10. To achieve a low-profile housing, the motor 6 is arranged towards one end of the device 1b and the spool 7 is mounted nearer to a centre of the housing 2 with a vertical rotational axis and a relatively large diameter. The spool rotational axis is parallel to the motor axis. The spool 7 has a relatively large diameter so that the number of wraps of cable on the spool 7 is reduced and the height of the spool 7 mounted with a vertical axis is minimised. The cable 5 wraps and unwraps to and from the spool 7 as the cable 5 is retracted into the housing 2 and extended from the housing 2 during use. The spool 7 is positioned to align the cable 5 with an opening through the housing 2. The cable extends from the spool 7 approximately horizontally and passes around a further pulley (pulley 201 in FIG. 4C, hidden from view in FIGS. 2A and 2B) to orient the cable from extending approximately horizontally within the housing to extend vertically through the opening in the housing 2.

The arrangement of motor, spool and pulley of the device of FIGS. 1A and 2A achieves a reduced width device compared to the motor, spool and belt drive arrangement of FIGS. 1B and 2B. However, the arrangement of FIGS. 1B and 2B achieves a shorter length device.

Again, with reference to FIGS. 2A and 2B, other components of each device 1a, 1b include a power supply 12, a motor controller 13 and a system controller 14. Preferably the power 12 supply is or comprises a (preferably rechargeable) battery to allow for portability so that the device 1a, 1b can be transported and used for a period of time without requiring an external power supply.

Preferably each motor 6 is controlled by the motor controller 13 to operate the motor 6 in a torque control mode to provide a force to the cable 5. In torque control mode, a position of the handle 4, motor 6 or spool 7 may not be communicated to the motor controller 13. In torque control mode, the motor controller 13 may control the motor 6 to provide a relatively constant force to the cable 5, regardless of handle or motor or spool position. As described above, when a user pulls on a handle 4 with a force (user force) greater than the force provided by the motor and spool to the cable 5 (motor force), the user lifts the handle 4 from the housing, unwrapping the cable 5 from the spool 7 against the motor force. When the user holds a handle 4 stationary, the user force is equal to the motor force and the motor and spool remain stationary. And when the user lowers the handle 4 the user force is less than the motor force, and the motor winds the cable 5 onto the spool 7. In torque control mode the motor operates to keep the cable under tension. In some embodiments, a tension or force sensor (not shown) may communicate a cable tension to the motor controller for use in the control of the motor.

When the user pulls the cable 5 to unwind the cable from the spool 7, the motor 6 may operate in a generator or brake mode to provide the controlled torque or force to the cable 5. When the motor 6 operates to rewind the cable 5 onto the spool 7, the motor 6 operates in a motor or driving mode. When in the generator or brake mode, the motor 6 generates electrical power. The device 1a, 1b may further comprise a recharging module (not shown) configured to apply the generated electrical power to the power supply 12 to recharge the battery. Alternatively, or additionally the device 1a, 1b may include an electrical resistance to dissipate some or all generated electrical power.

The system controller 14 provides control logic/routines for the device 1a, 1b. For example, the system controller 14 may be configured/programmed to provide one or more exercises for the user to perform. Preferably the controller 14 is configured to provide a plurality of exercises, and more preferably is configured to allow the user (via a Human Machine Interface) to select one or more exercises from a plurality of exercises. The controller 14 may determine an exercise routine based on user information. The system controller 14 may cause the motor controller 13 to control the motor 6 to provide a force to the cable 5 via the spool 7 to replicate traditional weightlifting exercises, for example, bicep curls or squats and the like. The controller 14 may allow the user to select a range of weight levels up to a maximum weight.

For example, the motor and spool may be configured to apply force to the cable 5 to present a maximum force of 20 kgf (200N) at the respective handle 4.

The system controller 14 may be configured to monitor the user's performance or use of the device while exercising via sensors and provide feedback to the user, for example audio feedback via an audio output device (e.g. speaker, not shown). Feedback may include coaching feedback to coach the user to improve exercise technique, and/or may provide motivational feedback based on user output, such as speed/pace of exercise, exercise duration, weight lifted etc.

The device 1a, 1b may include Human Machine Interface (not shown) such as a touch screen or display screen and user controls, to allow the user to provide one or more user inputs. In some embodiments, the HMI may be provided by a personal electronic device such as a smart phone to communicate with other components of the device 1a, 1b such as the system controller 14, the motor controller 13, and/or sensors. In the illustrated embodiments the system controller 14 is indicated as being part of the device 1a, 1b, however in some embodiments the system controller 14 may be provided by a separate device such as a personal electronic device (such as a smart phone) to communicate with the other components of the device 1a, 1b such as the motor controller 13, and/or sensors of the device.

Communication between a remote controller and/or HMI and the other components of the device may be provided by way of a communication protocol or network (for example Bluetooth, a cellular network, or another network optionally comprising various configurations and protocols including the Internet, intranets, virtual private networks, wide area networks, local networks, private networks using communication protocols proprietary to one or more companies—whether wired or wireless, or a combination thereof). A feedback device may also be provided via a separate remote device, again by a personal electronic device such a smart phone, for example.

The device 1a, 1b includes one or more sensors for use in the control of the device 1a, 1b and/or to provide feedback to the user, as mentioned above. For example, sensors may include a force (tension) sensor to provide an indication of force applied to the cable, a motor and/or spool position sensor, and/or one or more load cells to determine the weight of the user. FIG. 2A shows four load cells 15, each load cell provided adjacent a corner of the device 1b. Output from the load cell(s) 15 may be used to measure the user's weight or determine a user's position on the deck. The load cells may be used to determine the user's weight to suggest exercises, and/or be used to determine feedback/instruction to the user to stand on the deck correctly, or to activate the device 1a, 1b.

The device 1a, 1b comprises a position sensor (not shown) to detect a rotational position of the spool 7 and/or motor 6 and/or a datum point reference for the length of cable extending from the housing. The system controller 14 may be configured to determine a cable length extending from the device 1a, 1b based on one or more outputs from the position sensor. An example position sensor is a rotary encoder to determine a rotational position of the motor. The system controller may determine/calculate a length of cable extending from the housing based on the motor position, as described below.

A sensor arrangement 100, 200 is provided to detect two orthogonal angles of the cable 5 extending from the housing 2. The system controller 14 is configured to determine two orthogonal angles defining a trajectory of the cable 5 extending from the housing 2 based on one or more outputs from the sensor arrangement 100, 200. The system controller 14 is further configured to determine, from the two orthogonal angles and the cable length, a 3-dimensional position of the handle 4 (handle position) in a 3-dimensional space occupied by the user when using the device 1a, 1b. The handle position may be determined from the two angles and the cable length based on a spherical coordinate system.

The controller 14 may use the handle position in the control of the device 1b, 1b and/or to determine feedback to be provided to the user. For example, the controller 14 may determine coaching or user performance feedback based on the handle position, and/or may update exercise routines or make exercise suggestions to the user based on the handle position. The controller may determine and monitor the handle position real time during use, to provide real time feedback and/or updates to the user.

FIGS. 3A to 3G present one example sensor arrangement 100 for providing one or more outputs to the controller 14 from which the controller 14 determines two orthogonal angles $\theta$ and $\varphi$ defining a straight-line trajectory for the cable in the 3-dimensional space in which the cable extends from the device.

The sensor arrangement 100 comprises a lower pulley 101. The lower pulley 101 directs the cable 5 from below or within the housing 2 to extend above or external to the housing 2, i.e. the lower pulley 101 directs the cable from substantially horizontal to extend vertically above the housing 2. The pulley 101 rotates on a rotational axis to provide a low friction transition of the cable 5 from the housing 2. The pulley 101 is rotationally mounted on an axle (bolt) 102. The axle 102 is supported by a bracket or pair of brackets 103 (axle supports) which mount the sensor arrangement within the device.

A cable follower 104 is pivotally mounted to pivot about the rotational axis of the lower pulley 101. The cable 5 passes through the cable follower 104 after passing around the pulley 101 from the resistance mechanism 6, 7 to the handle 4, i.e. the cable follower is located on a 'handle-side' of the pulley 101. In the illustrated embodiment the follower 104 comprises an annular or tubular member through which the cable passes. Alternatively, the cable follower may comprise a ring member or a fork member through which the cable passes, and/or a pair of pulleys located either side of the cable. The follower 104 is carried on a frame 105 pivotally mounted to pivot on the rotational axis of the lower pulley 101. The frame 105 and lower pulley 101 may be mounted on the same (single) axle 102, as shown in FIG. 3B. Preferably bearings 106 are provided between the axle 102 and the pulley 101 and pivoting frame 105, or between the axle 102 and axle supports 103. The frame and/or axle presents a first pivot joint on which the cable follower pivots. The frame offsets the cable follower from the rotational axis of the pulley so that the cable extends from the pulley 101 to the cable follower 104 at a tangent to the pulley. The cable follower is offset from the rotational axis of the pulley by approximately the radius of the pulley, i.e. the radius of the pulley plus half the thickness (e.g. diameter) of the cable, so that the cable extends from the pulley at a tangent to the pulley.

The cable follower 104 has an internal dimension commensurate with an outer dimension of the cable cross section so that as the cable 5 moves in a lateral direction with respect to a longitudinal axis of the cable the cable follower 'follows' or remains coupled to the cable. The cable slides through the cable follower as the cable is extended and retracked by a user.

FIG. 3C shows the cable 5 turning through approximately 90 degrees about the lower pulley 101, with the cable 5 extending through the follower 104 oriented approximately vertically.

FIG. 3D shows the cable 5 turning through approximately 135 degrees about the lower pulley 101, with the cable 5 extending through the follower 104 at an angle to a vertical plane of about 45 degrees. One or more sensors 107 is/are coupled to the follower 104 and therefore also pivot, together with the follower 104 and pivoting frame 105, about the rotational axis of the lower pulley 101.

As shown by FIGS. 3C and 3D, the follower 104 couples the sensor 107 to the cable 5 so that the sensor 107 pivots about the pulley axis as the cable 5 wraps around the pulley and extends around pulley axis. Thus, the sensor 107 detects pivoting of the cable follower 104 as it pivots about the rotational axis of the pulley 101 and may be calibrated to provide an output indicative of an angle $\theta$ of the cable 5 extending in a vertical first plane. The first plane is perpendicular to the rotational axis of the lower pulley 101. The angle $\theta$ is an angle around the first pivot axis. Angle $\theta$ may be indicative of an angle of wrap of the cable 5 about the lower pulley 101, i.e. an angle equal to a pulley wrap angle minus 90 degrees.

The rotational axis of the pulley 101 is a first pivot axis (111 in FIGS. 3C and 3D) about which the pivoting frame 105 and the cable follower 104 pivots (i.e. an axis of the pulley axle). Additionally, the follower 104 is pivotally mounted to pivot about a second pivot axis (112 in FIGS. 3C to 3E), as shown in FIGS. 3E to 3G. In the illustrated embodiment, the follower 104 is pivotally mounted to the pivoting frame 105 to pivot relative to the pivoting frame 105. The cable follower 104 is connected to the pivoting frame 105 by an arm 108 extending between the cable follower 104 and the second pivot axis 112. The arm 108 is connected to the pivoting frame 105 via a second pivot joint (e.g. screw 109 in FIG. 3B). Preferably a bearing 106 is provided between the follower arm and the pivoting frame/second pivot joint.

The second pivot axis 112 is orthogonal to the first pivot axis 111. Thus, the sensor(s) 107 detects pivoting of the cable follower 104 as it pivots about the second pivot axis 112 and may be calibrated to provide an output indicative of an angle $\varphi$ of the cable 5 orthogonal to the angle $\theta$. The angle $\varphi$ is an angle around the second pivot axis. The sensor 107 shown in FIGS. 3B to 3D is omitted from FIGS. 3E to 3G, illustrating sensor mounting holes (113 in FIG. 3E).

Figure 3A:
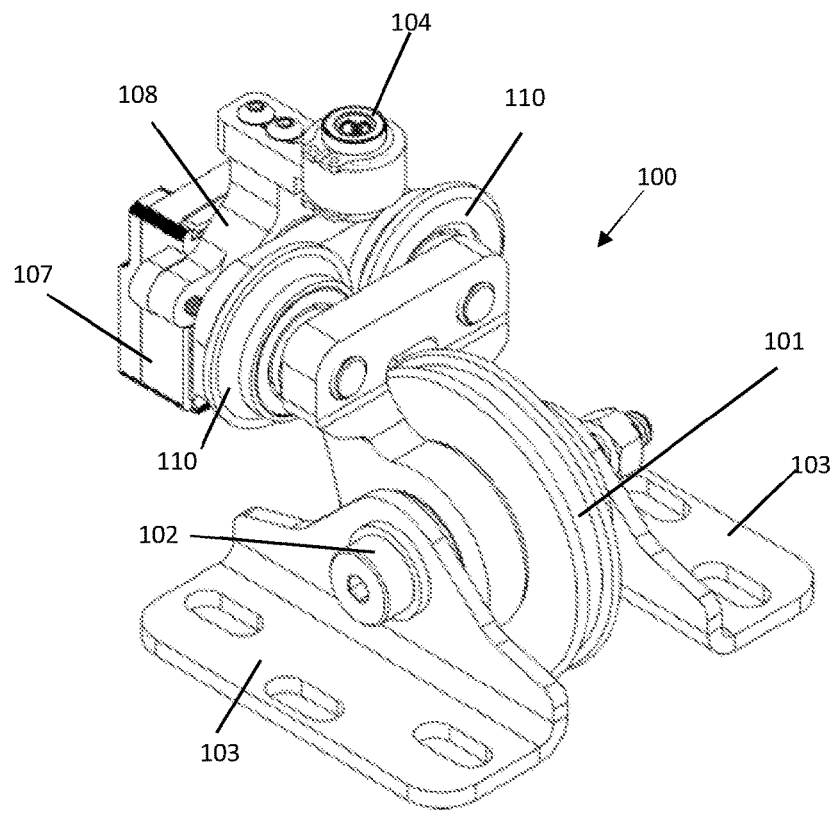
FIG. 3A illustrates a sensor arrangement for measuring or detecting two orthogonal angles of a cable of the device extending in a 3-dimensional space during use.
Figure 3B:
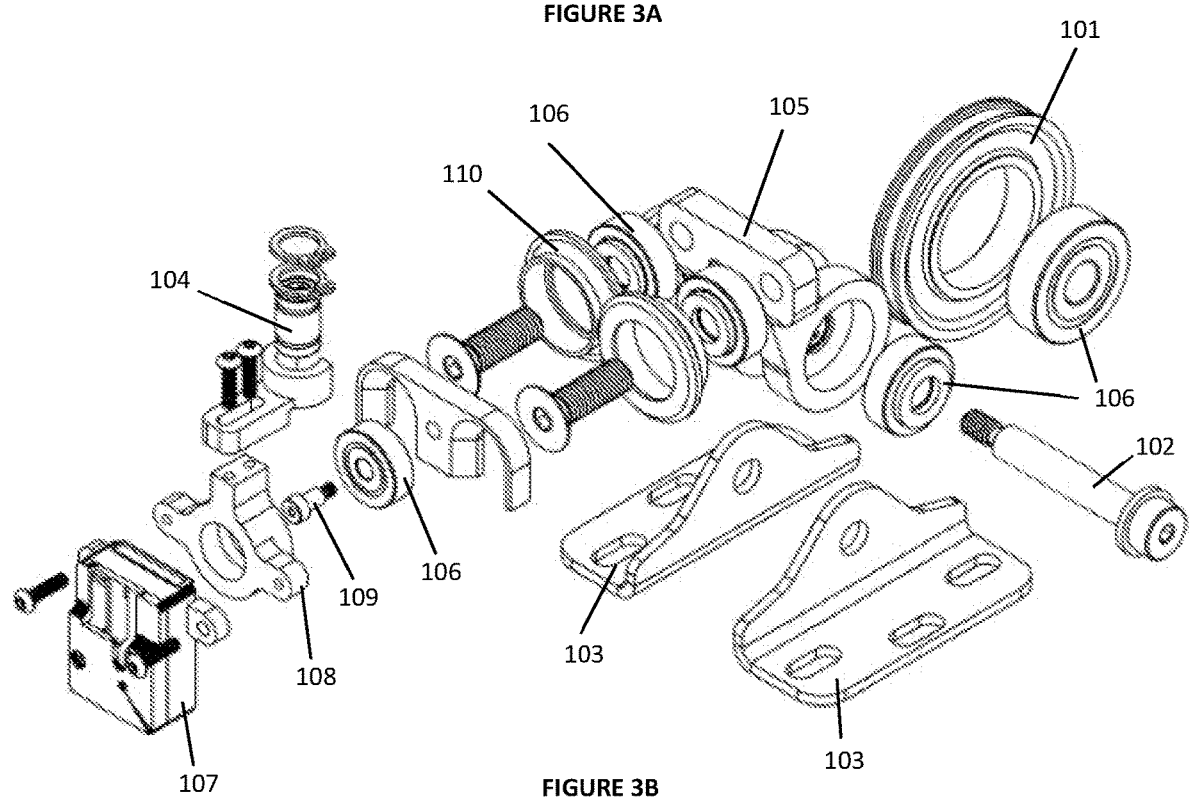
FIG. 3B provides an exploded view of the sensor arrangement of FIG. 3A.
Figure 3F:
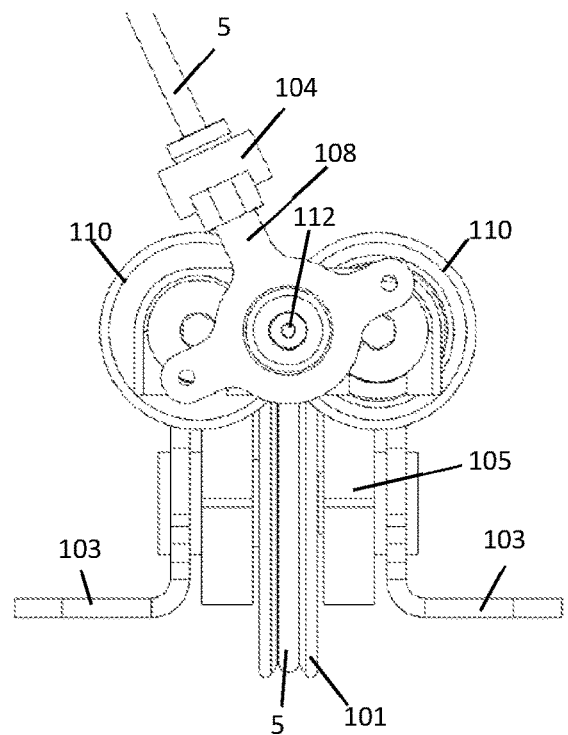
FIGS. 3F and 3G show the sensor arrangement of FIG. 3A pivoted in the vertical second plane either side of the vertical first plane (a sensor is omitted from FIGS. 3F and 3G.
Figure 3G:
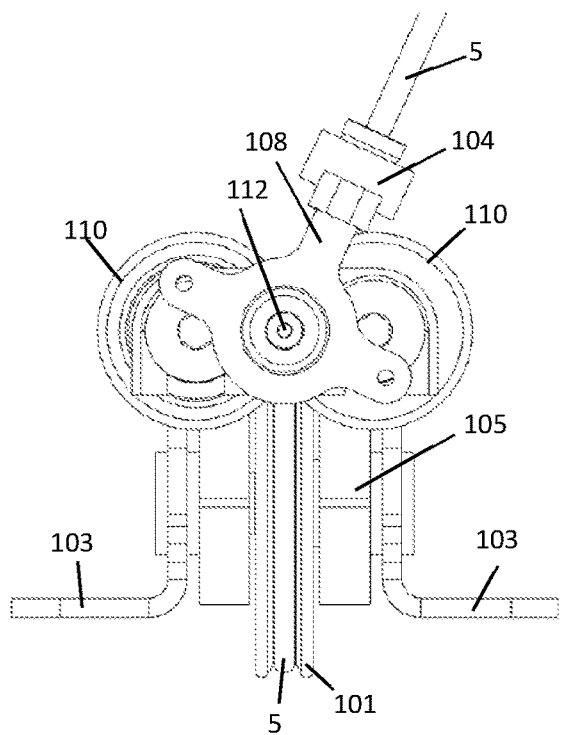

The sensor arrangement 100 of FIG. 3A to 3G also includes a pair of upper pulleys 110, each rotationally mounted to the pivoting frame 105. The cable 5 extends from the lower pulley 101 to pass between the upper pulleys 110. The upper pulleys 110 are spaced apart to provide a path between the two upper pulleys 110 for the cable 105 to pass. The cable path between the upper pulleys 110 is aligned with the lower pulley 101. The upper pulleys 110 are positioned between the cable follower 104 and the lower pulley 101. Each upper pulley 110 contacts an opposite side of the cable 5 to guide the cable 5 from the lower pulley 101 so that the cable 5 extends from the pulley 101 in plane with a central plane of the lower pulley 101, to maintain a angle of wrap of the cable 5 around the lower pulley 101. Additionally, or alternatively the lower pulley 101 has a circumferential groove for receiving the cable 5 so that the cable 5 remains wrapped around the lower pulley in plane with a central plane of the lower pulley 101. The second pivot axis 112 may be centred between rotational axes of the upper pulleys 110. The second pivot axis 112 is preferably aligned with a central plane of the lower pulley 101, as shown in FIGS. 3E to 3G.

In the embodiment of FIGS. 3A to 3G the one or more sensors may be an inertial measurement unit 107 comprising an accelerometer and gyroscope. A person skilled in the art will understand how the angles θ and φ may be determined from the outputs provided by an IMU. Other sensor types may be used, such as a hall effect sensor magnetically coupled to a magnetic element to measure each angle.

FIGS. 4A to 4H present another example sensor arrangement 200 for providing one or more outputs to the system controller 14 from which the controller 14 determines the two orthogonal angles defining a straight-line trajectory for the cable in the 3-dimensional space.

The sensor arrangement 200 comprises a pulley 201. The pulley 201 directs the cable 5 from below or within the housing 2 to above or external to the housing 2, i.e. the lower pulley directs the cable 5 from substantially horizontal to extend vertically above the housing 2. The pulley 201 rotates on a pulley rotational axis to provide a low friction transition of the cable 5 from the housing 2. The pulley is rotationally mounted on an axle (e.g. a shaft like that shown in FIG. 5B for the embodiment described below) that extends between two side covers 203. The side covers 203 form axle supports to support the axle. The side covers together form a second frame.

A cable follower 204 is pivotally mounted to pivot about the rotational axis of the lower pulley 201. The cable passes 5 through the cable follower 204 after passing around the pulley 201 from the resistance mechanism 6, 7 to the handle 4, i.e. the cable follower 204 is located on a 'handle-side' of the pulley 201. In the illustrated embodiment the follower 204 comprises an annular or tubular member through which the cable 5 passes. Alternatively, the cable follower may comprise a ring member or a fork member through which the cable passes. In the illustrated embodiment two upper pulleys 210 are also provided to direct the cable from the lower pulley 201 to the cable follower 204. The upper pulleys 210 are spaced apart along the cable. The upper pulleys 210 contact opposite sides of the cable 5 and may also form part of the cable follower. In some embodiments, the cable follower may comprise the two pulleys 210, each on an opposed side of the cable, alternatively or in addition to other means for laterally coupling the follower to the cable.

The cable follower 204 is carried on a frame 205 pivotally mounted to pivot on the rotational axis of the lower pulley 201. In the illustrated embodiment the frame 205 comprises two side plates that extend either side of the pulley 201. The frame 205 and lower pulley 201 may be mounted on the same (single) axle. Preferably bearings are provided between the axle and the pulley 201 and pivoting frame 205, or between the axle and axle supports 203. The frame and/or axle presents a first pivot joint on which the cable follower pivots.

The cable follower 204 has an internal dimension commensurate with an outer dimension of the cable cross section so that as the cable moves in a lateral direction with respect to a longitudinal axis of the cable the cable follower 'follows' or remains coupled to the cable. The cable slides through the cable follower as the cable is extended and tracked by a user.

Figure 4A:
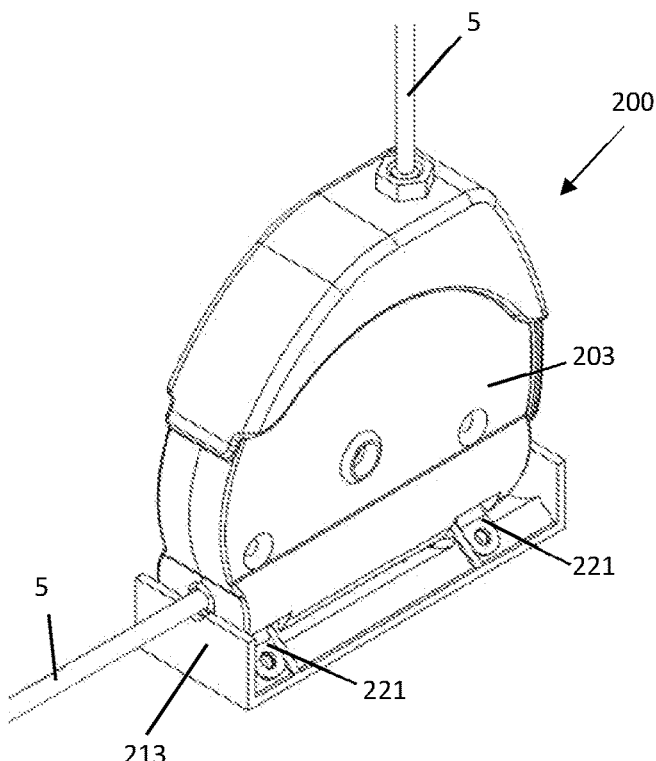
FIG. 4A illustrates a sensor arrangement for measuring or detecting two orthogonal angles of a cable of the device extending in a 3-dimensional space during use.
Figure 4B:
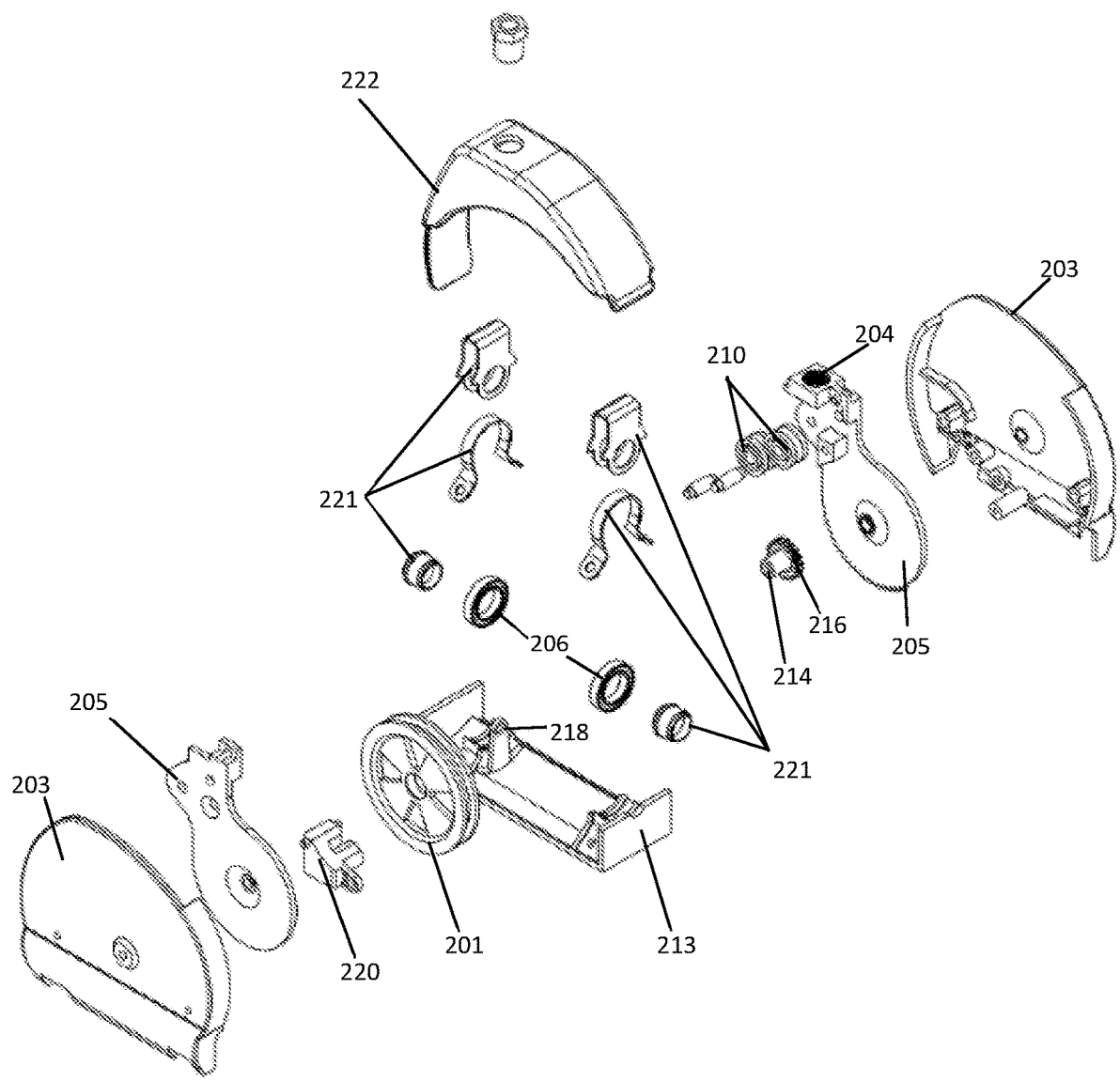
FIG. 4B provides an exploded view of the sensor arrangement of FIG. 4A.
Figure 4C:
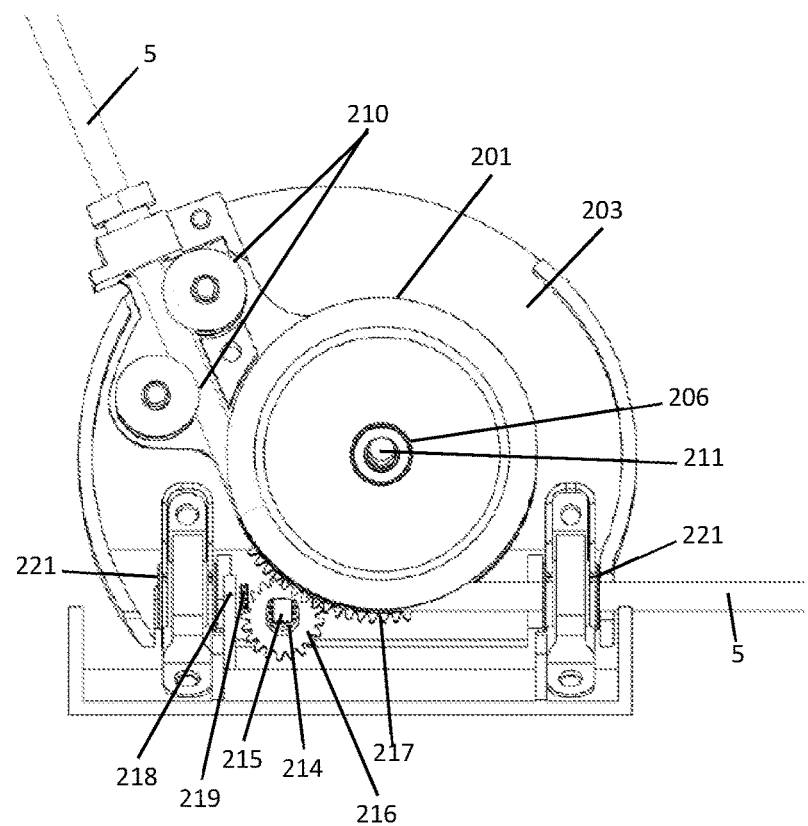
FIG. 4C provides a side view of the sensor arrangement of FIG. 4A with a side cover removed.
Figures 4D, 4E:
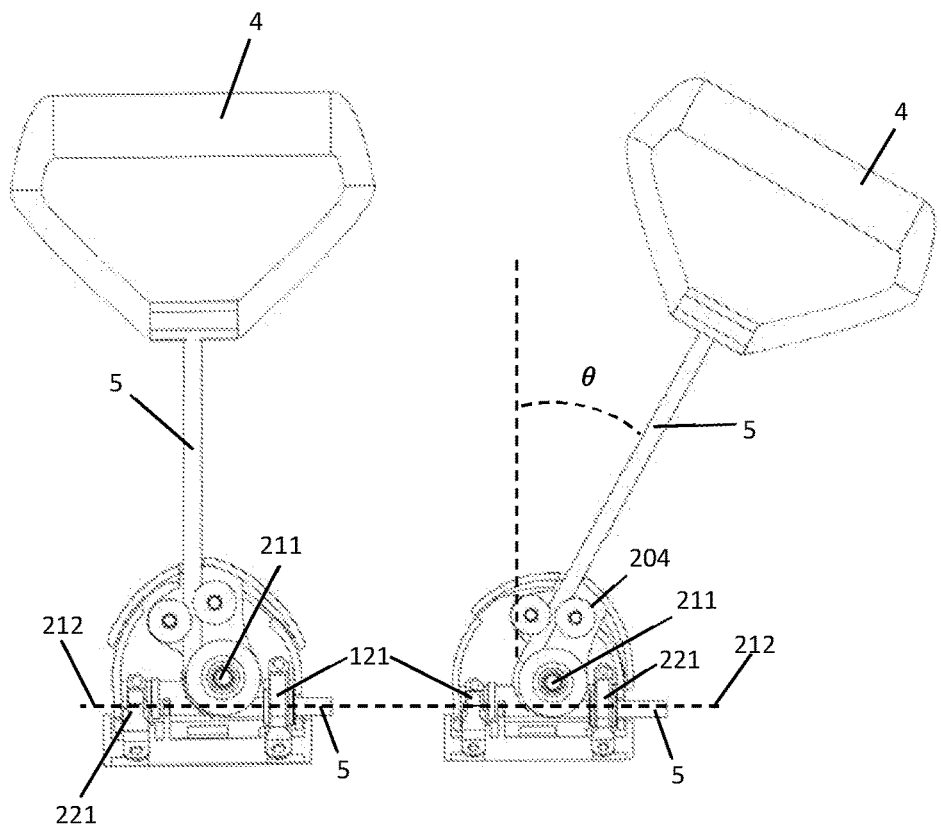
FIG. 4D provides a side view of the sensor arrangement of FIG. 4A with a side cover removed, and a cable and handle of the device with the cable extending vertically.
FIG. 4E provides a side view of the sensor arrangement of FIG. 4A with a side cover removed, and a cable and handle of the device with the sensor arrangement oriented with the cable extending at an angle to vertical in a vertical first plane. The cable extends in the first plane, and the first plane pivots about a second pivot axis of the sensor arrangement.

FIG. 4D shows the cable 5 turning through approximately 90 degrees about the lower pulley, with the cable extending through the follower 204 oriented approximately vertically.

FIG. 4E shows the cable 5 turning through approximately 120 degrees about the lower pulley, with the cable 5 extending through the follower 204 at an angle to a vertical plane of about 30 degrees.

A first sensor is provided to detect pivoting of the cable follower 204 about the rotational axis of the pulley. In the illustrated embodiment, the first sensor detects rotation of a sensor element. For example, the sensor element comprises a magnet 214 and the first sensor comprises a hall effect sensor 215 to detect rotation of the magnet. The magnet 214 is attached to a pinion gear 216 that engages a gear 217 coupled to the pivoting frame 205. The hall effect sensor detects rotation of the magnet and pinion as the pivoting frame 205 and cable follower 204 pivot about the pulley rotational axis. The gear 217 may include gear teeth integrally formed with the pivoting frame, i.e. in an edge of one of the side plates of the pivoting frame 205. In the illustrated embodiment, the hall effect sensor 215 is mounted to one or both side covers such that there is relative rotation between the magnet and hall effect sensor. One skilled in the art will understand that other sensor configurations or types are possible.

Thus, with reference to FIGS. 4D and 4E, the first sensor 214, 215 may be calibrated to provide an output indicative of an angle θ of the cable 5 in a first plane perpendicular to the rotational axis of the lower pulley 201. In FIGS. 4D and 4E, the sensor arrangement is oriented so that the first plane is vertical. However, the first plane pivots about the second pivot axis 212. The angle θ is an angle around the first pivot axis. As the cable follower 204 pivots about the rotational axis of the pulley, angle θ may be indicative of an angle of wrap of the cable 5 about the lower pulley 201, i.e. an angle equal to a pulley wrap angle minus 90 degrees.

The gearing between the cable follower 204 and the first sensor/sensor element 214 provided by the gears 216, 217 provides an increasing gear ratio from the cable follower to the first sensor/element. For example, in the illustrated embodiment, the gearing 216, 217 provides a ratio of 3, such that a 90 degree change in angle of the cable follower results in a 270 degree change in angle for the sensor element 214. This provides a greater resolution and accuracy compared to a sensor arrangement measuring the change in angle of the cable follower directly or at a gear ratio of 1. Furthermore, the gearing provides for a convenient location of the first sensor near to the second sensor (described below), providing for a more compact sensor arrangement 200.

Figure 4F:
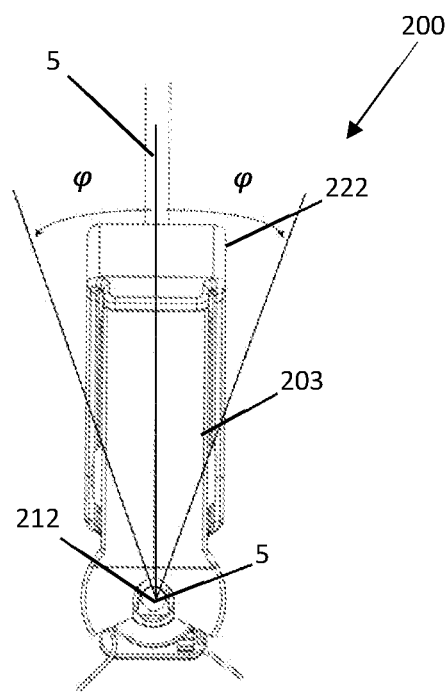
FIG. 4F provides an end view of the sensor arrangement of FIG. 4A and indicates an angle in a vertical second plane orthogonal to the first plane. The angle is between the first plane (or the pulley) and a vertical plane that intersects the first plane at the second pivot axis.
Figures 4G, 4H:
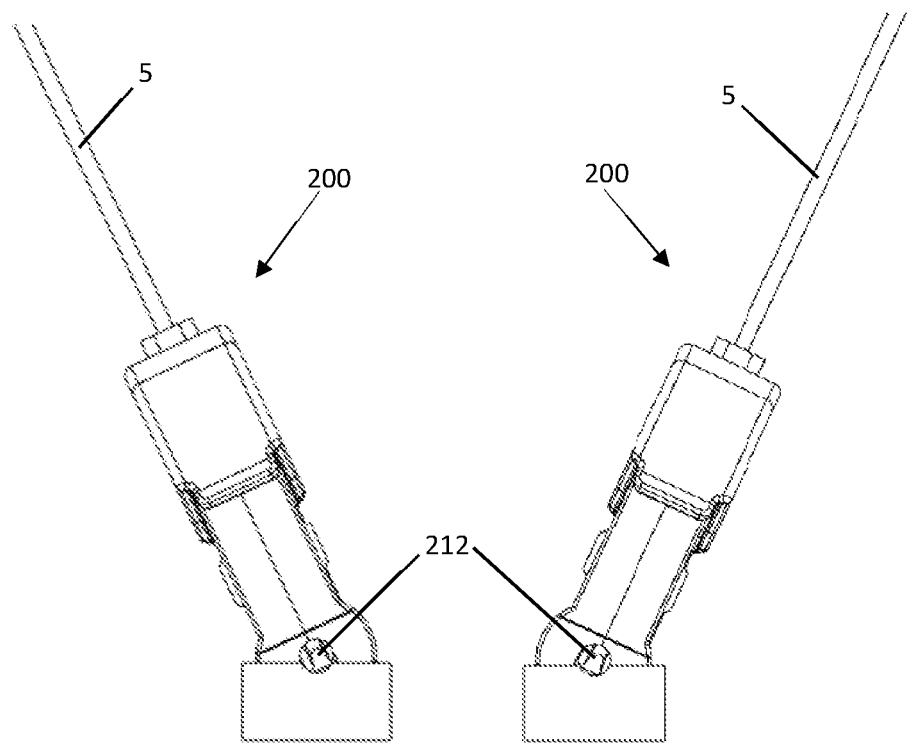
FIGS. 4G and 4H show the sensor arrangement of FIG. 4A pivoted about the second pivot axis either side of vertical.

The rotational axis of the pulley 201 is a first pivot axis 211 about which the pivoting frame 205 and cable follower 204 pivots (i.e. an axis of the pulley axle). Additionally, the lower pulley 201, pivoting frame 205 and cable follower 204 are pivotally mounted to pivot about a second pivot axis 212, as shown in FIGS. 4F to 4H.

The second pivot axis 212 is orthogonal to the first pivot axis 211. A second sensor is provided to detect pivoting of the cable follower 204, pivoting frame 205 and pulley 201 as they pivot about the second pivot axis 212. Thus, the second sensor may be calibrated to provide an output indicative of an angle φ orthogonal to the angle θ. The angle φ is an angle around the second pivot axis. The angle φ is in a vertical second plane orthogonal to the first plane and is between the pulley or first plane and a vertical plane that intersect the first plane at the second pivot axis.

In the illustrated embodiment, the second sensor detects rotation of a sensor element. For example, the sensor element comprises a magnet 218 and the second sensor comprises a hall effect sensor 219 to detect rotation of the magnet. The magnet 218 is attached to a base bracket 213 and the second sensor is attached to the axle supports or side covers 203. The axle supports/side covers 203 also pivot about the second pivot axis 212 together with the lower pulley 201, pivoting frame 205 and cable follower 204. With reference to FIG. 4B, the first and second sensors may be mounted together in a single sensor housing 220.

The axle supports 203 (side covers), pivoting frame 205 with cable follower 204 and the lower pulley 201 are pivotally mounted on one or more pivot mounts 221 to pivot about the second pivot axis 212. The pivot mounts 221 are mounted to the base bracket 213 which attaches the sensor arrangement 200 within the device 1b. Preferably each pivot mount 221 includes a bearing (206 in FIG. 4B). In the illustrated embodiment, the sensor arrangement comprises two spaced apart pivot mounts, with the axle supports 203 supported thereon and with the lower pulley mounted in between two pivot mounts 221. The pivot mounts provide the second pivot axis below the rotational axis of the lower pulley 201, and with the second pivot axis coincident with a central plane of the lower pulley. The pivot mounts 221 present a horizontal second pivot axis. The base bracket is located below the lower pulley to mount the sensor arrangement to a surface extending below the sensor arrangement. The arrangement of the pivot mounts provides for a compact sensor arrangement.

In the illustrated embodiment, the pivot mounts 221 are positioned so that the second pivot axis 212 is collinear or coincident with a longitudinal axis of the cable 5 extending from the lower pulley 201 on a resistance mechanism (motor) side of the pulley 201, i.e. the second pivot axis 212 is collinear with the cable 5 before it wraps around the pulley to extend then from the housing or frame of the device. Thus, the lower pulley 201, pivoting frame 205 and cable follower 204 are pivotally mounted to pivot on the longitudinal axis of the cable 5 extending from the lower pulley 201 on the resistance mechanism side of the lower pulley. A first one of the pivot mounts 221 is located on the resistance mechanism side of the lower pulley and is configured to receive the cable therethrough, as best shown in FIGS. 4C to 4F, i.e. the cable extends on a pivot axis of the pivot mount 221. The second pivot axis 212 is collinear with the pivot axis of the pivot mount 221. A second one of the pivot mounts 221 is located on the user interface side of the lower pulley. The cable does not pass through the second pivot mount since the cable wraps onto the lower pulley after passing through the first pivot mount.

The embodiment of FIGS. 4A to 4H includes a top cover 222. The cable passes through an aperture in the top cover. The top cover mores or slides on the side covers 203 as the cable angle in the first vertical plane changes. The top cover is coupled to the cable follower to move with the cable follower.

FIGS. 5A to 5H present another example sensor arrangement 300 for providing one or more outputs to the system controller 14 for determining the two orthogonal angles. The sensor arrangement 300 is shown in the resistance exercise device 1c illustrated in FIG. 6. The sensor arrangement 300 is configured to pivot about two angles as described above for the embodiment of FIGS. 4A to 4H. Various parts or features of the sensor arrangement 300 that are the same as or similar to parts or features of the arrangement of FIGS. 4A to 4H described above are not described again for brevity. Same or similar parts or features are identified by the same reference numerals appearing above but with a prefix of 3.

The sensor arrangement 300 comprises a pulley 3201 to direct the cable 5 from the housing 2 of the device 1c to above or external to the housing 2. A cable follower 3204 is pivotally mounted to pivot about the rotational axis of the pulley 3201. The cable passes 5 through the cable follower 3204 after passing around the pulley 3201 from the resistance mechanism 6, 7 to the handle 4, as described above. The cable follower 3204 is carried on a frame 3205 pivotally mounted to pivot on the rotational axis of the pulley 3201. In the illustrated embodiment the frame 3205 comprises a side plate that extends on one side of the pulley 3201.

The pulley is supported on axle 3223. In the illustrated embodiment, the frame 3205 and pulley 3201 are mounted on the same (single) axle. The axle is supported by axle supports 3203. The axle supports are integrally formed together in a second pivoting frame 3224. Preferably a bearing 3206 is provided between the axle 3223 and the pulley 3201, and/or between the axle 3223 and axle supports 3203. The frame 3205 and/or axle presents a first pivot joint on which the cable follower 3205 pivots.

Figure 5A:
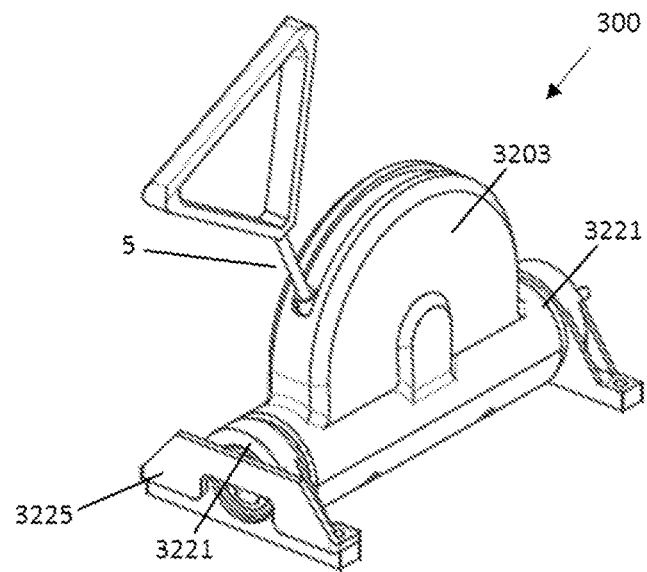
FIG. 5A illustrates a sensor arrangement for measuring or detecting two orthogonal angles of a cable of the device extending in a 3-dimensional space during use.
Figure 5B:
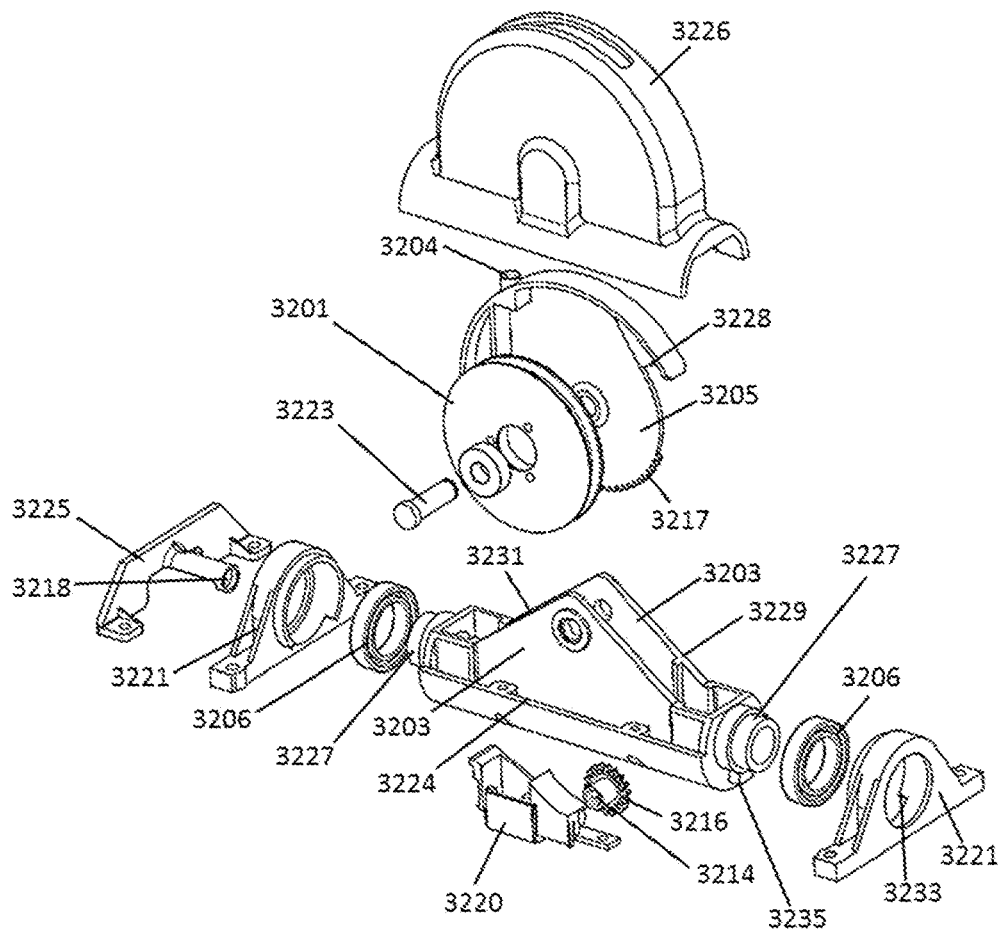
FIG. 5B provides an exploded view of the sensor arrangement of FIG. 5A.
Figure 5C:
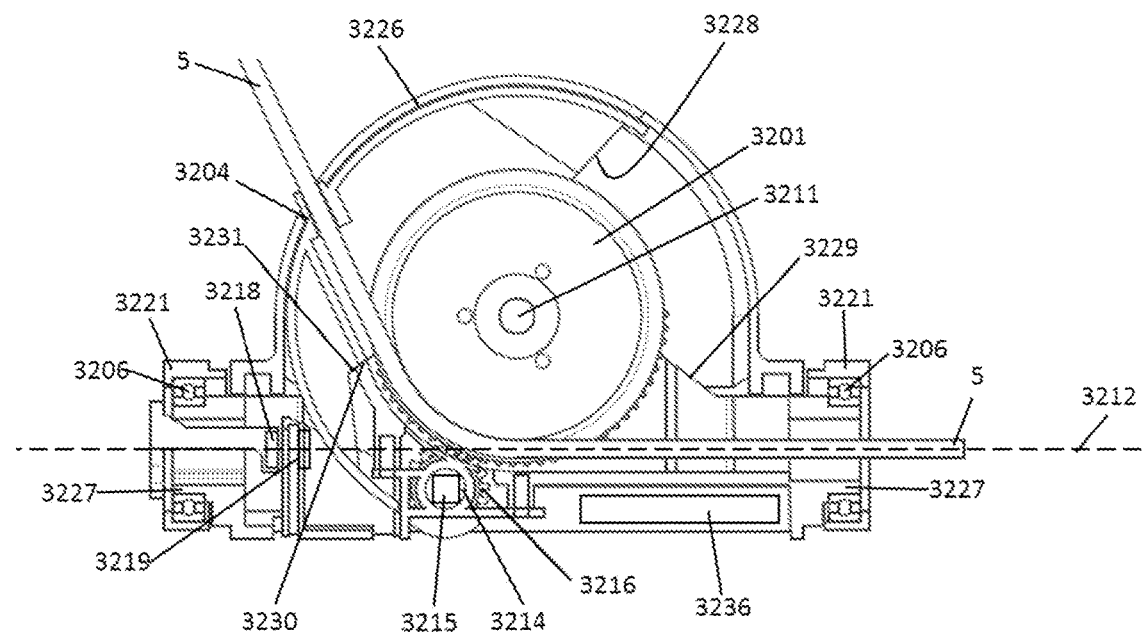
FIG. 5C provides a side sectional view on a section line through a center of the sensor arrangement of FIG. 5A, with the sensor arrangement oriented with the cable extending at an angle to vertical in a vertical first plane, and with the sensor arrangement at an angular limit. The cable extends in the first plane, and the first plane pivots about a second pivot axis of the sensor arrangement.
Figure 5D:
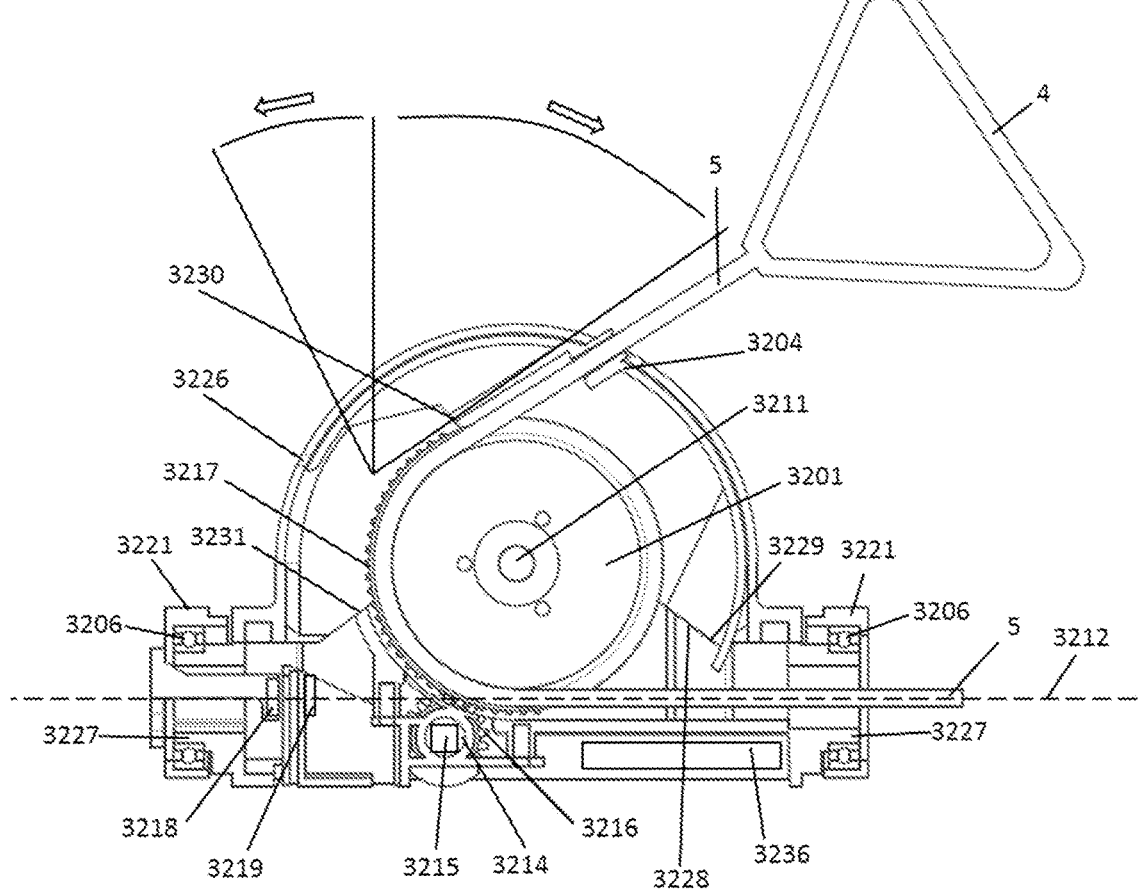
FIG. 5D provides the same section view as FIG. 5C but with the arrangement at a second angular limit.

FIG. 5C shows the cable 5 turning through approximately 60 degrees about the pulley, with the cable 5 extending through the follower 204 at an angle to a vertical plane of about −30 degrees. FIG. 5D shows the cable 5 turning through approximately 150 degrees about the pulley, with the cable 5 extending through the follower 204 at an angle to a vertical plane of about 60 degrees.

A first sensor is provided to detect pivoting of the cable follower 3204 about the rotational axis of the pulley. In the illustrated embodiment, the first sensor detects rotation of a sensor element. The sensor element comprises a magnet 3214 and the first sensor comprises a hall effect sensor 3215 to detect rotation of the magnet. The magnet 3214 is attached to a pinion gear 3216 that engages a gear 3217 coupled to the pivoting frame 3205, as described above for the earlier embodiment 200. The gear 3217 includes gear teeth formed in an edge of the pivoting frame 3205. In the illustrated embodiment, the hall effect sensor 215 is mounted to the axle supports/second frame 3203, 3224 such that there is relative rotation between the magnet and hall effect sensor. Thus, the first sensor 3214, 3215 may be calibrated to provide an output indicative of an angle θ of the cable 5.

Figure 5E:
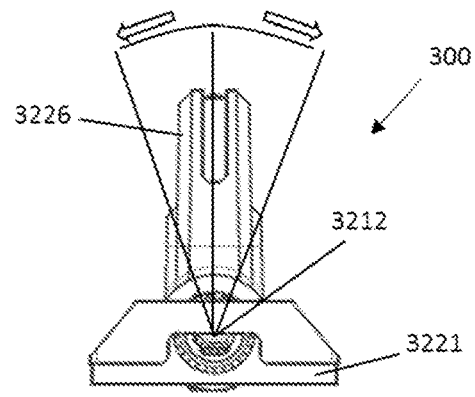
FIG. 5E provides an end view of the sensor arrangement of FIG. 5A and indicates an angle in a vertical second plane orthogonal to the first plane. The angle is between the first plane (or the pulley) and a vertical plane that intersects the first plane at the second pivot axis.

The rotational axis of the pulley 3201 is the first pivot axis 3211 about which the pivoting frame 3205 and cable follower 3204 pivots (i.e. an axis of the pulley axle). Additionally, the pulley 3201, pivoting frame 3205 and cable follower 3204 are pivotally mounted to pivot about the second pivot axis 3212 orthogonal to the first pivot axis 211, as shown in FIG. 5E. A second sensor is provided to detect pivoting of the cable follower 3204, pivoting frame 3205 and pulley 3201 as they pivot about the second pivot axis 3212. Thus, the second sensor may be calibrated to provide an output indicative of the angle φ of the cable 5 orthogonal to angle θ.

In the illustrated embodiment, the second sensor detects rotation of a sensor element. For example, the sensor element comprises a magnet 3218 and the second sensor comprises a hall effect sensor 3219 to detect rotation of the magnet. The magnet 3218 is attached to a bracket 3225 and the second sensor is attached to the axle supports/second frame 3203, 3224. With reference to FIG. 5B, the first and second sensors may be mounted together in a single sensor housing 3220 mounted to the axle supports/second frame 3203, 3224.

The axle supports 3203, pivoting frame 3205 with cable follower 3204 and the pulley 3201 are pivotally mounted on two spaced apart pivot mounts 3221 to pivot about the second pivot axis 3212. The pivot mounts 3221 attach the sensor arrangement 300 within the device 1c. The axle supports 3203 are supported on the pivot mounts with the pulley 3201 mounted in between the two pivot mounts 3221. The pivot mounts provide the second pivot axis below the rotational axis of the pulley 3201, and with the second pivot axis coincident with a central plane of the pulley. The pivot mounts 221 present a horizontal second pivot axis. The pivot mounts 221 each provide a base to mount the sensor arrangement 300 to a surface extending below the sensor arrangement 300. The arrangement of the pivot mounts provides for a compact sensor arrangement. The arrangement of the pivot mounts allows the sensor arrangement 300 to be mounted close to a surface on which it is mounted to achieve a low assembly height for the device 1c.

The pivot mounts 3221 are positioned so that the second pivot axis 3212 is collinear (coincident) with a longitudinal axis of the cable 5 extending from the pulley 3201 on a resistance mechanism (motor) side of the pulley 3201 as described above for the earlier embodiment 200, with a first one of the pivot mounts configured to receive the cable therethrough. The second frame 3224 comprises a pair of aligned spigots 3227, with each spigot supported at a respective pivot mount 3221 to pivot thereon. The spigot received in the first one of the pivot mounts includes a passage to receive the cable therethrough to pass through the pivot mount and spigot to the pulley 3201.

Figure 5F:
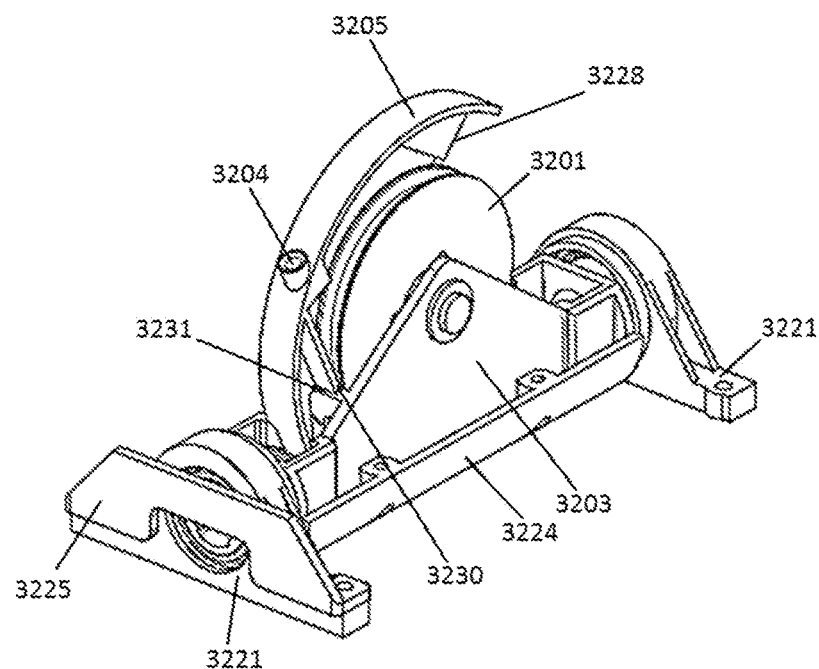
FIG. 5F illustrates the sensor arrangement of FIG. 5A with a cover removed.
Figure 5G:
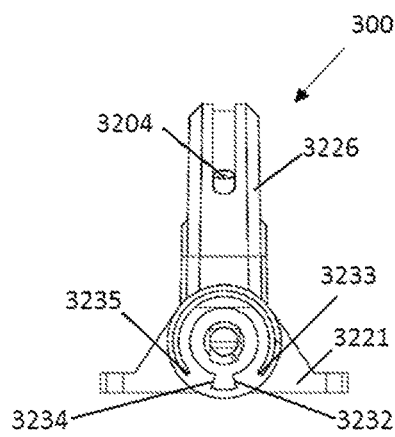
FIG. 5G provides an end sectional view on a section line through a bearing housing to illustrate an angle limit stop for pivoting about the second pivot axis.
Figure 5H:
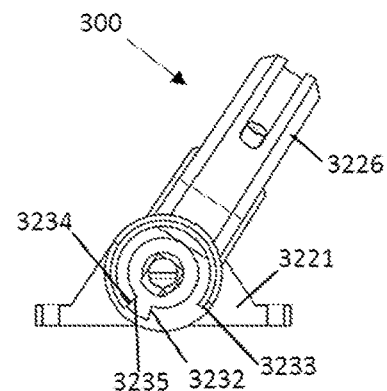
FIG. 5H provides the same section view as in FIG. 5G but with the sensor assembly pivoted about the second pivot axis at an angular limit.

The sensor arrangement 300 comprises limit stops to limit the amount of pivoting of the cable follower about the first pivot axis 3211 and/or second pivot axis 3212. With reference to FIGS. 5C, 5D and 5F, the pivoting frame 3205 comprises a first surface 3228 to abut a corresponding surface 3229 on at least one axle support 3203 or the second frame 3224 to limit the pivoting of the cable follower 3204 in a first direction of rotation about the first pivot axis 3211, and a second surface 3230 to abut a corresponding surface 3231 on at least one axle support 3203 or the second frame 3224 to limit the pivoting of the cable follower 3204 in a second opposite direction of rotation about the first pivot axis 3211. FIG. 5D shows the first surface 3228 abutting corresponding surface 3229, and FIGS. 5C and 5F show the second surface 3230 abutting corresponding surface 3231. With reference to FIGS. 5G and 5H, the axle supports 3203 or second frame 3224 comprises a first surface 3232 to abut a corresponding surface 3233 on at least one pivot mount 3221 to limit the pivoting of the cable follower 3204 in a first direction of rotation about the second pivot axis 3212, and a second surface 3234 to abut a corresponding surface 3235 on at least one pivot mount 3221 to limit the pivoting of the cable follower 3204 in a second opposite direction of rotation about the second pivot axis 3212. Alternatively, or additionally, the housing 2 of the device 1c may present surfaces 16 to limit the amount of pivoting of the sensor arrangement 300 about the second pivot axis 3212, by contacting an outer surface of the sensor arrangement 300.

The sensor arrangement 300 may comprise a weight or ballast so that the centre of gravity of the pivoting assembly comprising the pulley, pivoting frame and cable follower that pivots on the pivot mounts about the second pivot axis is located at the second pivot axis. With the centre of gravity or balance point for the pivoting assembly located at second pivot axis, when no tension is applied by a user to the cable, the pivoting assembly including the pulley does not fall or drop to one side or other. The pulley remains in its last orientation about the second pivot axis when tension is removed from the cable, to improve the user's experience when using the device. For example, to balance the pivoting assembly, the second frame 3224 may carry a weight 3236 indicated schematically in FIG. 5D. The weight 3236 is carried by the second frame 3224 below the second pivot axis 3212 so that a centre of gravity of the second frame and components carried by the second frame is at the second pivot axis.

The embodiment of FIGS. 5A to 5H includes a top cover 3226. The cable passes through a slot in the top cover. Unlike the earlier embodiment 200, the top cover does not move with the cable follower. The top cover 3226 is fixed to the axle supports/second frame 3203, 3224 to pivot about the second pivot axis 3212. The second frame together with the top cover provide a housing for containing the internal components of the sensor arrangement 300. This provides for robust protection of the sensitive sensor components of the arrangement 300. Any force or loading applied to the top cover 3226 is transmitted to the pivot mounts and bearings 3206 and not to other more sensitive components of the sensor arrangement such as the gears and sensor elements. The sensitive components of the sensor arrangement are isolated from the top cover. The pivoting frame 3205 comprise a circumferentially extending flange to cover the slot in the top cover 3226 so that the internal components of the sensor arrangement are substantially fully enclosed.

Figure 7:
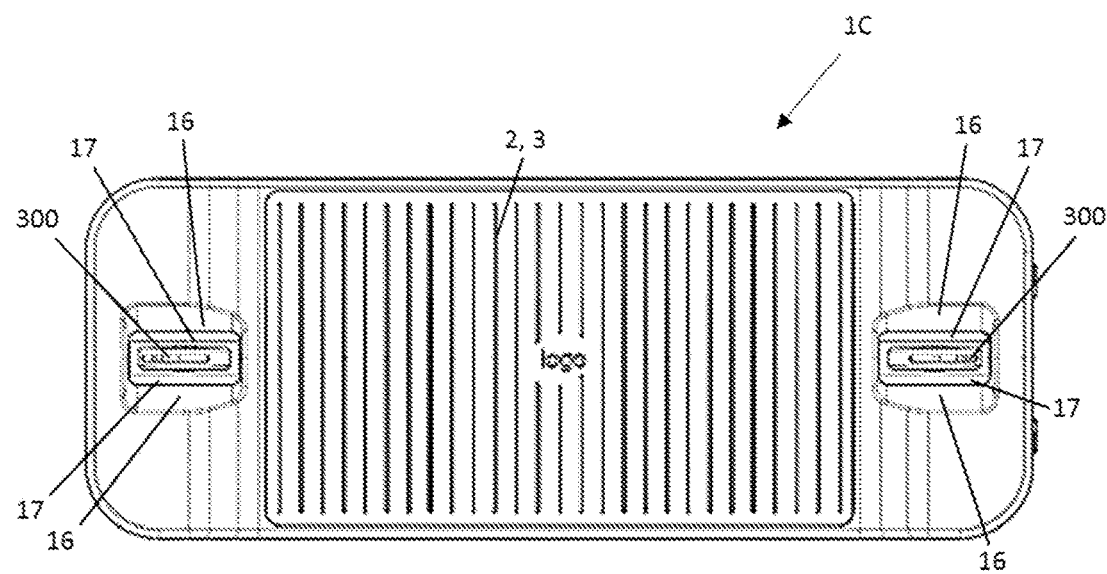
FIG. 7 is a top view of the device of FIG. 6.
Figure 8:
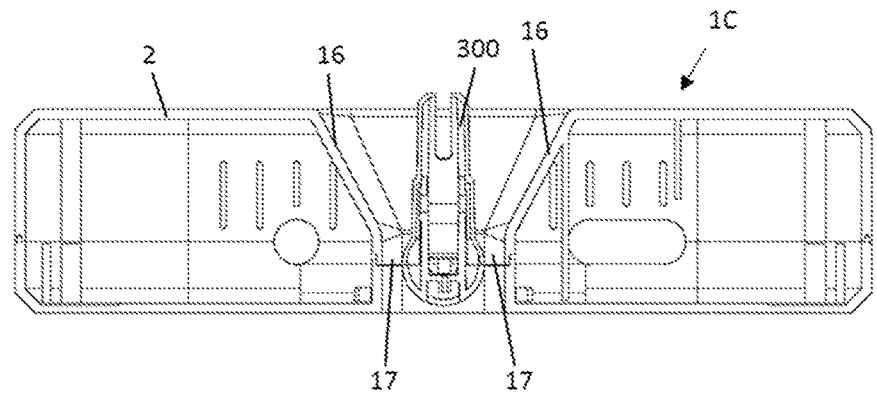
FIG. 8 is a sectional view of the device of FIG. 6 on a sectional line through a rotational axis of a pulley of the sensor arrangement. The pulley is omitted from FIG. 8.

With reference to FIGS. 7 and 8, the sensor arrangement 300 is mounted to the housing 2 of the device to be visible to an outside of the housing. The sensor arrangement 300 is located in a recess in a top of the housing 2. The outer cover 3226 is substantially visible to the outside of the device. However, the bearing mounts 3221 are housed inside/covered by the housing 2 of the device 1c. The sensor arrangement 300 extends between two opposed sides 17 of the recess of the housing, extending from the housing via an aperture 18 in each side of the recess. The recess includes an open area 19 on either side of the sensor arrangement 300 that presents a passage through the device 1c so that any debris or liquid entering the recess can pass through the recess to below the device 1c. This arrangement reduces a risk of debris or liquids entering the housing 2 of the device 1c or collecting around the sensor arrangement 300. The bearing mounts 3221 are also protected by being located within the device housing 2.

Figure 6:
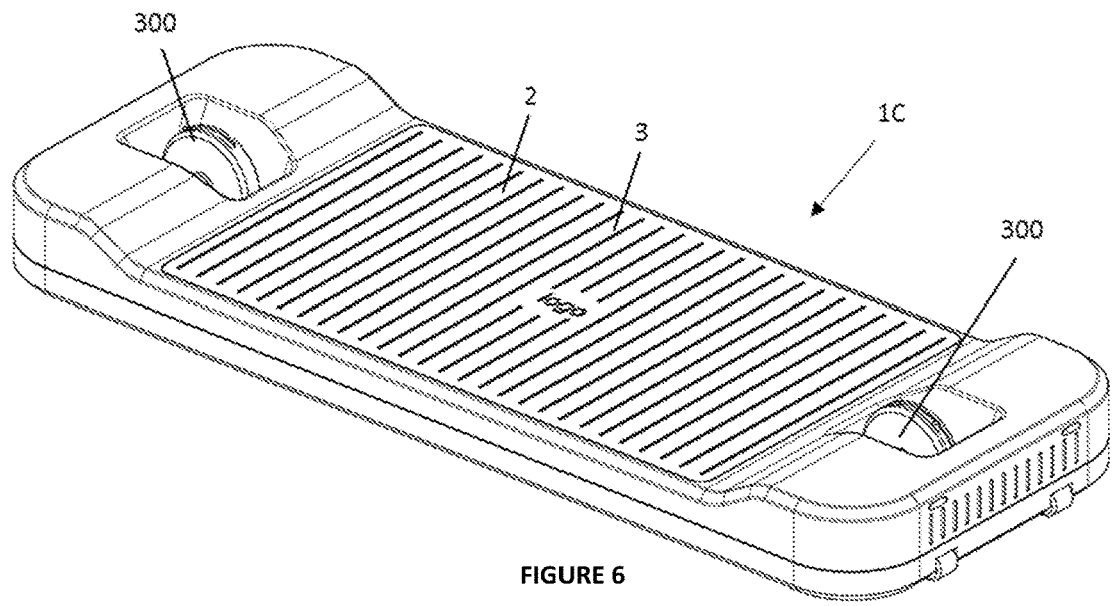
FIG. 6 illustrates another embodiment of an exercise device according to an aspect of the present invention comprising the sensor arrangement of FIG. 5A. Handles and cables are omitted from this view.

The device 1a of FIGS. 1A and 2A as illustrated includes the sensor arrangement 100, the device 1b of FIGS. 2A and 2B as illustrated includes the sensor arrangement 200, and the device 1c of FIGS. 6 to 8 as illustrated includes the sensor arrangement 300. However, one skilled in the art will understand that either device 1a, 1b and 1c may include the sensor arrangement 100, 200 or 300.

As described above, the system controller is configured to determine the handle position in the 3 dimension space from orthogonal angles θ, φ and a length of the cable extending in the 3-dimensional space, these three data points presenting three coordinates in a spherical coordinate system. It is to be understood that that the length of the cable extending from the device/housing may be represented as a length of cable extending from the spool or other cable length datum point within the device. An example calculation for determining the handle position with reference to the embodiment of FIGS. 3A to 3G is provided below.

With reference to FIG. 9, the system controller is configured to calculate a 3-dimensional coordinate position for the handle in the 3-dimensional space in which the handle is movable during use. In a preferred embodiment the controller is configured to determine an (x, y, z) cartesian coordinate for the handle position P. In the illustrated example the x-dimension is in a side-to-side direction of the device (extending between the handles), the y-direction is in a front-to-back direction of the device, and the z-direction vertical.

One may expect the calculation to determine the (x, y, z) coordinates for the handle position from the cable length extending from the device and the two orthogonal angles θ, φ to be relatively straight forward, the relevant equations based on a spherical coordinate system being:

$$x = L\sin(\theta)\cos(\varphi)$$

$$y = L\sin(\varphi)$$

$$z = L\cos(\theta)\cos(\varphi)$$

However, the inventors identified a significant error in the calculation of the cable length using the above equations dependent on the cable wrap angle on the lower pulley. For example, with the cable extending horizontally from the pulley (θ=90 degrees), as the cable is rotated upwards towards vertical (reducing θ), the cable unwraps from the pulley which results in the cable extending further from the pulley in the 3-dimensional space, even though the motor remains stationary. Conversely, with the cable extending vertically (θ=0), as the cable is rotated downwards (increasing θ), more cable is wrapped onto the pulley, reducing the length of cable extending in the 3-dimensional space, again even though the motor is stationary. Thus a 'functional' or 'effective' length of the cable in the 3-dimensional space changes with the angle of wrap of the cable about the pulley that is not measured by a change in motor position.

Figure 11:
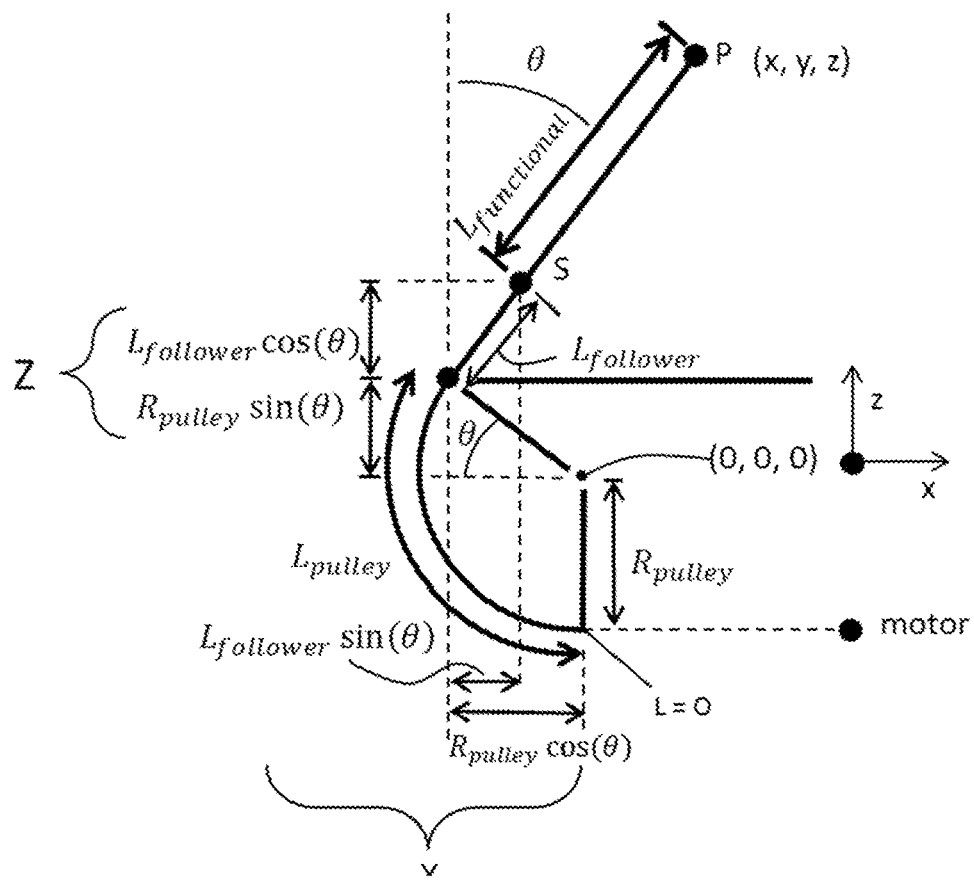
FIG. 11 provides a diagram representing a side view of the sensor arrangement of FIG. 3A (corresponding to FIGS. 3D and 10) identifying parameters used in equations disclosed herein for determining a position of the handle in a 3-dimensional space.

To account for the wrap of the cable about the lower pulley, the inventors have determined a calculation method whereby the cable length extending from the device is determined from a bottom of the pulley 101, and wherein the origin (0, 0, 0) for the cartesian coordinate system is at or with respect to the rotational axis 111 of the pulley 101. Preferably the origin for the cartesian system is centred on or is with respect to a central plane of the pulley 101 (i.e. the central plane perpendicular to the rotational axis 111. The following equations are derivable based on this definition for the coordinate system:

$$L_{functional} = L_{motor} - R_{pulley}(\theta + \pi/2) - L_{follower}$$

$$x = L_{functional}\sin(\theta)\cos(\varphi) - R_{pulley}\cos(\theta) + L_{follower}\sin(\theta)$$

$$y = L_{functional}\sin(\varphi)$$

$$z = L_{functional}\cos(\theta)\cos(\varphi) + R_{pulley}\sin(\theta) + L_{follower}\cos(\theta)$$

Wherein with reference to FIGS. 10 and 11, the variables are:

$R_{pulley}$ the radius of the lower pulley;

$L_{follower}$ the length of the cable extending between the pulley and an origin (S in FIG. 11) for the sensor measuring the angles of the cable follower, for example the length of the cable extending from the pulley to the second pivot axis where the angle sensor origin S is at the second pivot axis;

$L_{functional}$ distance from the origin S for the sensor measuring the angles of the cable follower to the handle position measured along a line of the cable (i.e. tangent to the cable), for example the distance from the second pivot axis to a position (P in FIGS. 10 and 11) on the handle to be gripped by a user;

$L_{motor}$ the length of the cable extending from a datum (zero) point of the cable to the handle, in this example, from a vertical bottom of the pulley 101 to the handle;

θ the angle (the first angle) in the Z-X plane (a vertical first plane) between a plane tangential to the lower pulley in which the cable extends in the 3-dimensional space and the Z-Y plane (a vertical second plane) orthogonal to the Z-X plane.

φ the angle (the second angle), in the plane tangential to the lower pulley, between the cable extending in the 3-dimensional space and the Z-X plane (the vertical first plane).

The length of the cable extending from the origin of the sensor S measuring the cable angles is incorporated in the above calculation. This is important since the measured angles θ and φ extend from that point. In the example calculation the sensor origin S is provided at the second pivot axis 112, however the sensor origin may be in an alternative position.

In the above calculation the length of the cable from the motor is given as the length of the cable extending from the bottom of the pulley 101, wherein a length of the cable 5 between the bottom of the pulley to the spool is considered constant. One skilled in the art will understand an alternative reference point may be used. The length of the cable extending from the bottom of the pulley or other reference point may be calculated based on an output from a position sensor providing a position of the motor and/or spool, a number of revolutions of the spool or motor from a calibrated motor or spool zero position, and the spool diameter.

The inventors identified a further error in the calculation of the handle position is introduced where the sensor arrangement includes upper pulleys 110. The error is introduced by a discrepancy between the cable angle and the measured angle of the cable follower.

Figure 12:
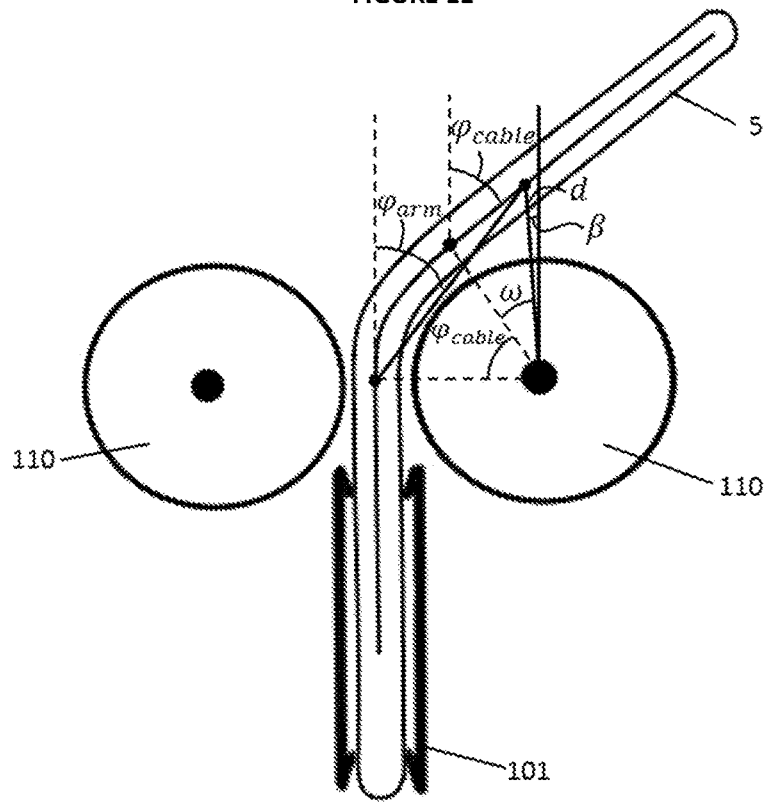
FIG. 12 provides a diagram representing an end view of the sensor arrangement of FIG. 3A (corresponding to FIG. 3E) identifying parameters used in equations disclosed herein for determining a position of the handle in a 3-dimensional space.

As shown in FIG. 12, the second pivot axis 112 is in line with rotational axes of the pair of upper pulleys. Where the second pivot axis 112 is in line with the rotational axes of the upper pulleys 110, the angle of the follower 104 is slightly less than the angle of the cable 5 extending from the follower 104 due to the cable slightly wrapping around one of the upper pulleys 110. Therefore, the measured angle of the follower 104 is less than the angle φ of the cable 5 in the 3-dimensional space, introducing an error in the calculation of the handle position based on the two orthogonal angles and the cable length.

To account for this error in the angle φ, a relationship between the follower angle and the cable angle is derived based on a known (measured) angle of the cable follower and an estimated cable angle, as follows.

With reference to FIG. 12, firstly, a position x, y for the cable follower is calculated based on a distance from the cable follower to the second pivot axis as an origin, however an origin can be chosen from any point. $r_{pulley}$ is the radius of the upper pulley:

$$x = r_{pulley}\cos(\varphi_{arm})$$

$$y = r_{pulley}\sin(\varphi_{arm})$$

A distance d from a middle of the upper pulley that the cable wraps around to the cable follower x, y position is determined:

$$d = \sqrt{(x - r_{pulley})^2 + y^2}$$

An intermediate angle β is determined:

$$\beta = \arcsin((r-x)/d)$$

A further intermediate angle ω is determined, where $L_f$ is the length of the follower arm from the second pivot axis to the x, y position of the cable follower.

$$\omega = \arccos(r_{pulley}/L_f)$$

Finally, the angle of the cable is calculated as:

$$\varphi_{cable} = 90 - \beta - \omega$$

In some embodiments, the second pivot axis may be positioned on a lower pulley side of a line extending between the rotational axes of the upper pulleys. For example, the second pivot axis 112 may be located between a line extending between the rotational axes of the upper pulleys 110 and the rotational axis 111 of the lower pulley 101. For example, in the embodiment of FIGS. 3A to 3G, the pivoting frame 105, and the arm 108 connecting the cable follower 104 to the pivoting frame 105, may be configured so that the second pivot axis 112 is collinear with the cable 5 extending on a resistance mechanism side of the lower pulley.

One skilled in the art will understand a calculation of the cable length and therefore handle position may also take into account a wrap of the cable around an upper pulley. The above equations are provided by way of example.

Figure 13:
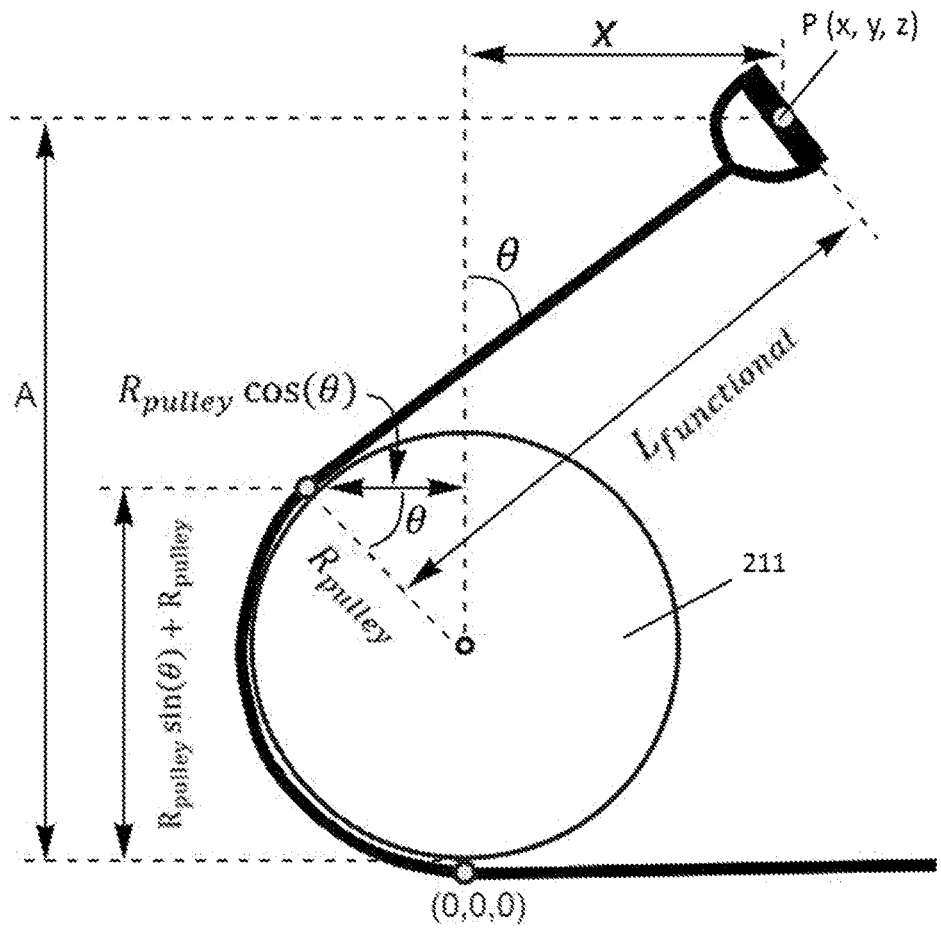
FIG. 13 provides a diagram representing a side view of the sensor arrangement of FIGS. 4A and 5A (corresponding to FIGS. 4E and 5D) identifying parameters used in equations disclosed herein for determining a position of the handle in a 3-dimensional space.
Figure 14:
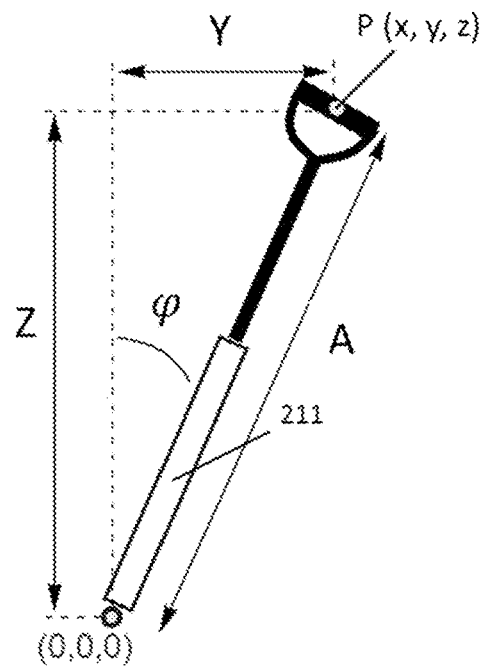
FIG. 14 provides a diagram representing an end view of the sensor arrangement of FIGS. 4A and 5A (corresponding to FIGS. 4F and 5E) identifying parameters used in equations disclosed herein for determining a position of the handle in a 3-dimensional space.

The above handle position calculations are provided by way of example with respect to the sensor arrangement of FIGS. 3A to 3G. An alternative preferred calculation for determining the cable length extending from the device for the embodiments of FIGS. 4A to 4H and 5A to 5H is provided below with reference to FIGS. 13 and 14. The origin (0, 0, 0) for the coordinate system is at or with respect to the vertical bottom of the pulley 201, 3201 (i.e. a position on the circumference of the pulley vertically below the pulley centre). Preferably the origin for the cartesian system is centred on or with respect to a central plane of the pulley 201, 3201 (i.e. the central plane perpendicular to the rotational axis 211, 3211. The following equations are derivable based on this definition for the coordinate system:

$$L_{functional} = L_{motor} - R_{pulley}(\theta + \pi/2)$$

$$A = L_{functional} \cos(\theta) + R_{pulley} \sin(\theta) + R_{pulley}$$

$$x = L_{functional} \sin(\theta) - R_{pulley} \cos(\theta)$$

$$y = A \sin(\varphi) = [L_{functional} \cos(\theta) + R_{pulley} \sin(\theta) + R_{pulley}] \sin(\varphi)$$

$$z = A \cos(\varphi) = [L_{functional} \cos(\theta) + R_{pulley} \sin(\theta) + R_{pulley}] \cos(\varphi)$$

Wherein with reference to FIGS. 13 and 14, the variables are:

$R_{pulley}$ the radius of the pulley 201, 3201;

$L_{functional}$ length of the cable from the pulley to the handle position (i.e. P in FIG. 13) measured along a line of the cable (i.e. a tangent to the pulley);

$L_{motor}$ the length of the cable extending from a datum (zero) point of the cable to the handle, in this example, from a vertical bottom of the pulley 201, 3201 to the handle. In this example, the origin (0, 0, 0) for the coordinate system and the datum (zero) point of the cable are at the same point;

θ the angle (the first angle) of the cable extending in a first plane orthogonal to the rotational axis of the pulley. The first plane pivots about the second pivot axis. The first plane is vertical when the pulley is oriented vertically.

φ angle (the second angle) from vertical in the Z-Y plane (the vertical second plane). The angle is between the first plane (or the pulley) and a vertical plane that intersects the first plane at the second pivot axis.

The sensor arrangements are described herein with reference to an exercise device comprising an electrically powered resistance mechanism (electric motor and spool). One skilled in the art will appreciate the described sensor arrangements 100, 200, 300 may be used in any exercise device comprising a handle and cord attached to a resistance mechanism, including traditional weightlifting devices comprising a stack of metal plates, or exercise devices that utilise the user's body weight to generate resistance.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. A personal exercise device comprising:
   a user interface to be moved by a user in a 3-dimensional space when using the personal exercise device;
   a resistance mechanism to generate a force;
   a cable coupled between the user interface and the resistance mechanism to transmit the force from the resistance mechanism to the user interface; and
   a sensor arrangement configured to detect two orthogonal angles to define a trajectory of the cable extending in the 3-dimensional space during use, the sensor arrangement comprising:
      a pulley to direct the cable as it extends from the personal exercise device during use, the pulley comprising a rotational axis;
      a cable follower through which the cable passes, the cable follower pivotally mounted to pivot about a first pivot axis and about a second pivot axis, the second pivot axis orthogonal to the first pivot axis, and wherein the first pivot axis is collinear with the rotational axis of the pulley, and
      one or more sensors configured to detect pivoting of the cable follower about the first and second pivot axes and provide one or more outputs indicative of the two orthogonal angles to define the trajectory of the cable extending in the 3-dimensional space.

2. The personal exercise device as claimed in claim 1, wherein the cable follower is mounted on a pivoting frame, the pivoting frame pivotally mounted to pivot on the rotational axis of the pulley.

3. The personal exercise device as claimed in claim 2, wherein the pivoting frame and the pulley are mounted together on a single axle.

4. The personal exercise device as claimed in claim 2, wherein the cable follower is pivotally mounted to the pivoting frame to pivot relative to the pivoting frame about the second pivot axis.

5. The personal exercise device as claimed in claim 4, wherein the second pivot axis is aligned with a central plane of the pulley.

6. The personal exercise device as claimed in claim 2, wherein the pulley, pivoting frame and cable follower are pivotally mounted on one or more pivot mounts to pivot about the second pivot axis.

7. The personal exercise device as claimed in claim 6, wherein the pulley and pivoting frame are mounted on an axle supported by one or more axle supports, and the one or more axle supports are mounted to the one or more pivot mounts to pivot on the second pivot axis.

8. The personal exercise device as claimed in claim 1, wherein a first angle of the two orthogonal angles is an angle of the cable follower in a first plane perpendicular to the rotational axis of the pulley.

9. The personal exercise device as claimed in claim 8, wherein the first plane pivots on the second pivot axis with the pulley.

10. The personal exercise device as claimed in claim 8, wherein the first angle is indicative of an angle of wrap of the cable about the pulley.

11. The personal exercise device as claimed in claim 8, wherein a second angle of the two orthogonal angles is an angle of the cable follower in a vertical second plane orthogonal to the first plane, between the first plane and a vertical plane that intersects the first plane at the second pivot axis.

12. The personal exercise device as claimed in any one of claim 11, wherein the one or more sensors comprises:
a first sensor configured to detect the pivoting of the cable follower about the first pivot axis and provide an output indicative of the first angle, and
a second sensor configured to detect the pivoting of the cable follower about the second pivot axis and provide an output indicative of the second angle.

13. The personal exercise device as claimed in claim 12, wherein the sensor arrangement further comprises gears between the pivoting frame and the first sensor or a sensor element sensed by the first sensor, the gears providing an increasing gear ratio from the pivoting frame to the first sensor or the sensor element.

14. The personal exercise device as claimed in claim 1, wherein the sensor arrangement further comprises limit stops to limit an amount of pivoting of the cable follower about the first pivot axis and/or second pivot axis.

15. The personal exercise device as claimed in claim 1, wherein the second pivot axis is collinear with the cable extending on a resistance mechanism side of the pulley.

16. The personal exercise device as claimed in claim 1, wherein:
the resistance mechanism comprises an electric motor and a spool rotationally driven by the electric motor, and wherein the cable is coupled to the spool; and
the personal exercise device comprises a motor controller configured to operate the electric motor to generate the force.

17. The personal exercise device as claimed in claim 1, further comprising a position sensor and a system controller configured to determine:
a length of cable extending in the 3-dimensional space based on one or more outputs from the position sensor;
the two orthogonal angles based on the one or more outputs from the one or more sensors; and
a position of the user interface in the 3-dimensional space during use based on the length of the cable and the two orthogonal angles.

18. The personal exercise device as claimed in claim 17, wherein the system controller is configured to provide feedback to the user via a feedback device based on the position of the user interface in the 3-dimensional space.

19. The personal exercise device as claimed in claim 1, wherein the sensor arrangement is mounted within a recess in a top of a housing of the personal exercise device.

20. A method for determining a position of a user interface of a personal exercise device in a 3-dimensional space during use, the personal exercise device comprising:
the user interface, a resistance mechanism to generate a force, a cable coupled between the user interface and the resistance mechanism to transmit the force from the resistance mechanism to the user interface, and a pulley directing the cable from the personal exercise device in the 3-dimensional space, and a cable follower through which the cable passes, the cable follower pivotally mounted to pivot about a first pivot axis and a second pivot axis, the second pivot axis orthogonal to the first pivot axis;
wherein the method comprises:
determining a length of cable extending in the 3-dimensional space;
determining two orthogonal angles to define a trajectory of the cable extending in the 3-dimensional space based on pivoting of the cable follower about the first and second pivot axes; and
determining the position of the user interface in the 3-dimensional space during use based on the length of the cable and the two orthogonal angles.

21. The method of claim 20, wherein the first pivot axis is collinear with a rotational axis of the pulley.

* * * * *